(12) United States Patent
Chen et al.

(10) Patent No.: US 8,003,392 B2
(45) Date of Patent: Aug. 23, 2011

(54) DIAGNOSTIC TEST FOR THE DETECTION OF EARLY STAGE LIVER CANCER

(75) Inventors: Cuiying Chen, Balegem (BE); Roland H. Contreras, Merelbeke (BE)

(73) Assignees: VIB VZW, Gent (BE); Universiteit Gent, Gent (BE)

( * ) Notice: Subject to any disclaimer, the term of this patent is extended or adjusted under 35 U.S.C. 154(b) by 0 days.

(21) Appl. No.: 12/452,103

(22) PCT Filed: Jun. 11, 2008

(86) PCT No.: PCT/EP2008/057325
§ 371 (c)(1),
(2), (4) Date: Mar. 16, 2010

(87) PCT Pub. No.: WO2008/152070
PCT Pub. Date: Dec. 18, 2008

(65) Prior Publication Data
US 2011/0136240 A9    Jun. 9, 2011

Related U.S. Application Data

(60) Provisional application No. 60/944,029, filed on Jun. 14, 2007.

(51) Int. Cl.
*G01N 33/48* (2006.01)
(52) U.S. Cl. .......... 436/64; 436/63; 436/86; 436/94
(58) Field of Classification Search .......... 436/63, 436/64, 86, 87, 94; 422/430
See application file for complete search history.

(56) References Cited

U.S. PATENT DOCUMENTS

| | | | |
|---|---|---|---|
| 2004/0147033 A1* | 7/2004 | Shriver et al. | 436/87 |
| 2005/0112691 A1* | 5/2005 | Callewaert et al. | 435/7.1 |
| 2006/0014294 A1* | 1/2006 | Contreras et al. | 436/86 |
| 2008/0318332 A1* | 12/2008 | Mechref et al. | 436/106 |

FOREIGN PATENT DOCUMENTS

| | | |
|---|---|---|
| WO | WO 2006/121892 A | 11/2006 |
| WO | WO 2008/152070 A1 | 12/2008 |
| WO | 2009/013538 * | 1/2009 |
| WO | 2009/075883 * | 6/2009 |
| WO | 2009/117666 * | 9/2009 |

OTHER PUBLICATIONS

Callewaert et al., Noninvasive diagnosis of liver cirrhosis using DNA sequencer-based total serum protein glycomics, Nature Medicine, Nature Publishing Group, Apr. 1, 2004, pp. 429-34, vol. 10, No. 4, New York, NY, US.
Paradis et al., Identification of a New Marker of Hepatocellular Carcinoma by Serum Protein Profiling of Patients With Chronic Liver Disease, Hepatology, 2005, pp. 40-47, vol. 41, No. 1.
Comunale et al., Proteomic Analysis of Serum Associated Fucosylated Glycoproteins in the Development of Primary Hepatocellular Carcinoma, Journal of Proteome Research, 2006, pp. 308-15, vol. 5, No. 2.
Liu et al., N-Glycomic Changes in Hepatocellular Carcinoma Patients with Liver Cirrhosis Induced by Hepatitis B Virus, Hepatology, 2007, pp. 1426-1435, vol. 46, No. 5.
PCT International Search Report, PCT/EP2008/057325, dated Sep. 23, 20008.
U.S. Appl. No. 12/231,168, filed Aug. 28, 2008, Contreras et al., Improved Protein Secretion in Eukaryotic Cells.
U.S. Appl. No. 11/792,203, filed Aug. 6, 2007, Chen et al., Aging Biomarker.
U.S. Appl. No. 12/225,396, filed Sep. 17, 2008, Contreras et al., Novel Vaccine Against Trypanosoma Cruzi Infection.
European Office Action of Application No. 08 760 873.3-2404; dated Nov. 3, 2010.
Response to Office action dated Feb. 24, 2011.

* cited by examiner

*Primary Examiner* — Maureen Wallenhorst
(74) *Attorney, Agent, or Firm* — TraskBritt, P.C.

(57) ABSTRACT

Described are methods and kits to detect early stage hepatocellular carcinoma or a change in the gradation of hepatocellular carcinoma in mammals. The diagnostic marker is based on the profiling and identification of diagnostic carbohydrates present in a body fluid, such as blood serum.

Figure 1:
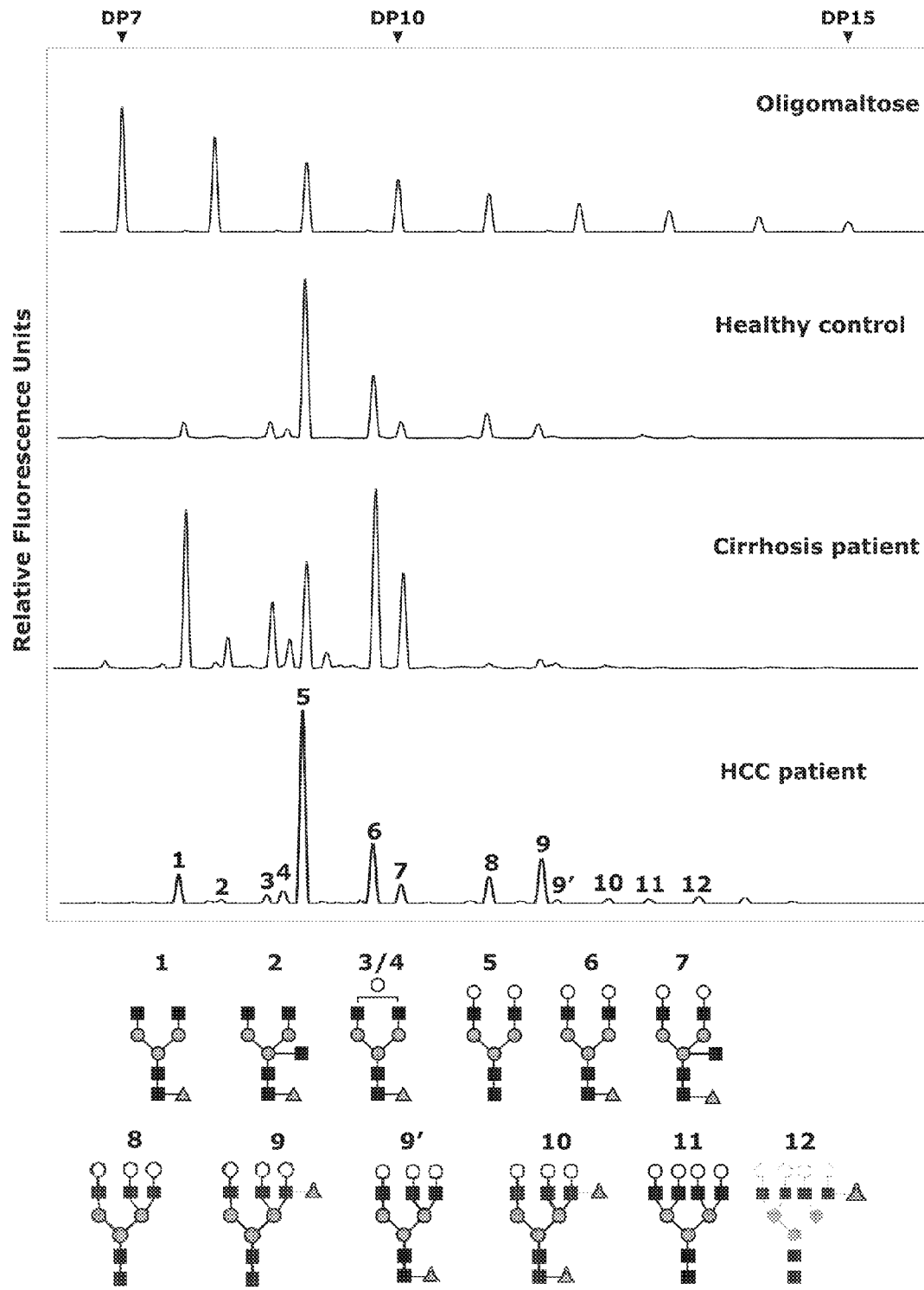

7 Claims, 13 Drawing Sheets

DIAGNOSTIC TEST FOR THE DETECTION OF EARLY STAGE LIVER CANCER

CROSS-REFERENCE TO RELATED APPLICATION(S)

This application is the national stage under 35 U.S.C. §371 of PCT/EP2008/057325, filed Jun. 11, 2008, designating the United States of America and published in English as WO 2008/152070 A1 on Dec. 18, 2008, and claims the benefit under Article 8 of the Patent Cooperation Treaty and 35 U.S.C. §119(e) to U.S. Provisional Patent Application U.S. Ser. No. 60/944,029, filed Jun. 14, 2007.

FIELD OF THE INVENTION

The invention provides methods and kits to detect early stage hepatocellular carcinoma or a change in the gradation of hepatocellular carcinoma in mammals. The diagnostic marker is based on the profiling and identification of diagnostic carbohydrates present in a body fluid such as blood serum.

BACKGROUND OF THE INVENTION

Hepatocellular carcinoma (HCC) or liver cancer is one of the most common cancers and one of the leading causes of death worldwide (1). HCC arises most commonly in cirrhotic livers following infection with hepatitis B virus (HBV) or hepatitis C virus (HCV) (2, 3). Indeed, liver cirrhosis is an important cause of death and a major risk factor for development of HCC, and 60-80% of HCC had been preceded by cirrhosis (4). Therefore, screening cirrhosis populations for early stage HCC can reduce mortality. Various imaging techniques are used to diagnose HCC, e.g. ultrasonography, computed tomographic scanning and magnetic resonance imaging (5, 6). However, these techniques cannot distinguish benign hepatic lesions, such as dysplastic nodules and cirrhotic macronodules, from HCC. For a long time serum tumor markers have been used as an effective method for detecting malignant tumors (7-9), and they could be valuable supplements to ultrasonography and computed tomography in the diagnosis of HCC (10-12). Serum AFP (alpha-fetoprotein) is the only serum marker that is widely used for diagnosis and follow-up of HCC (13, 14). A recent meta-analysis showed that the sensitivity and specificity of AFP varied widely, and that these variations could not be entirely attributed to the threshold effect of the different cutoff levels used (15). Other improved serological markers, whether used alone or together with others, are needed for early detection of HCC. Most serum N-linked glycoproteins are synthesized by the liver and B-lymphocytes. Any changes in serum total N-glycans could reflect alteration of liver or B-lymphocyte physiology. Because the sugar chains of glycoproteins are important for maintaining the ordered "social behavior" of differentiated cells in multicellular organisms, alterations in the sugar chains contribute to the molecular basis of abnormalities such as invasion of tumor cells into the surrounding tissues and their metastasis. Alterations in the N-linked sugar chains are indeed found in various tumors (6, 16-18). Until recently, the use of glycomics in diagnosis has been limited by the lack of appropriate analytical techniques, but at least in the case of the serum N-glycome this has been overcome (19, 20). In the present invention we evaluated the use of blood serum N-glycan fingerprinting as a tool for diagnosis of hepatocellular carcinoma (HCC) in patients with cirrhosis induced by hepatitis B virus. In particular, we found that branch alpha (1,3)-fucosylated glycans were more abundant in HCC patients than in cirrhosis patients, fibrosis patients and healthy blood donors, whereas bisecting GlcNac (N-acetylglucosamine)-core alpha (1,6)-fucosylated glycans were elevated in cirrhosis patients. The concentration of these two glycan-forms and the log ratio thereof (renamed as GlycoHCCTest) was associated with the tumor stage of liver cancer.

FIGURE LEGENDS

FIG. 1: The upper panel shows malto-oligosaccharides as sugar mass reference. The number of glucose units (DP, degree of polymerization) in these structures is indicated. A typical desialylated N-glycan profile from total serum protein is shown in the lower panels. The structures of the N-glycan peaks are shown below the panels.

Peak 1 is an agalacto, core-α-1,6-fucosylated biantennary glycan (NGA2F), peak 2 is an agalacto, core-α-1,6-fucosylated bisecting biantennary (NGA2FB), peak 3 and peak 4 are a single agalacto, core-α-1,6-fucosylated biantennarys (NG1A2F), peak 5 is a bigalacto, biantennary glycan (NA2), peak 6 is a bigalacto, core-α-1,6-fucosylated biantennary (NA2F), peak 7 is a bigalacto, core-α-1,6-fucosylated bisecting biantennary (NA2FB), peak 8 is a tri-antennary (NA3), peak 9 is a branching α-1,3-fucosylated tri-antennary (NA3Fb), peak 10 is a core-α-1,6 fucosylated tri-antennary (NA3Fc), peak 11 is a tetra-galacto, tetra-antennary (NA4), and peak 12 is a branching α-1,3-fucosylated tetra-antennary (NA4Fb). The symbols used in the structural formulas are: ■ β-linked N-acetylglucosamine (GlcNAc); ○ β-linked galactose; ▲ α-1,3/6-linked fucose; and • α/β-linked mannose.

Figure 2:
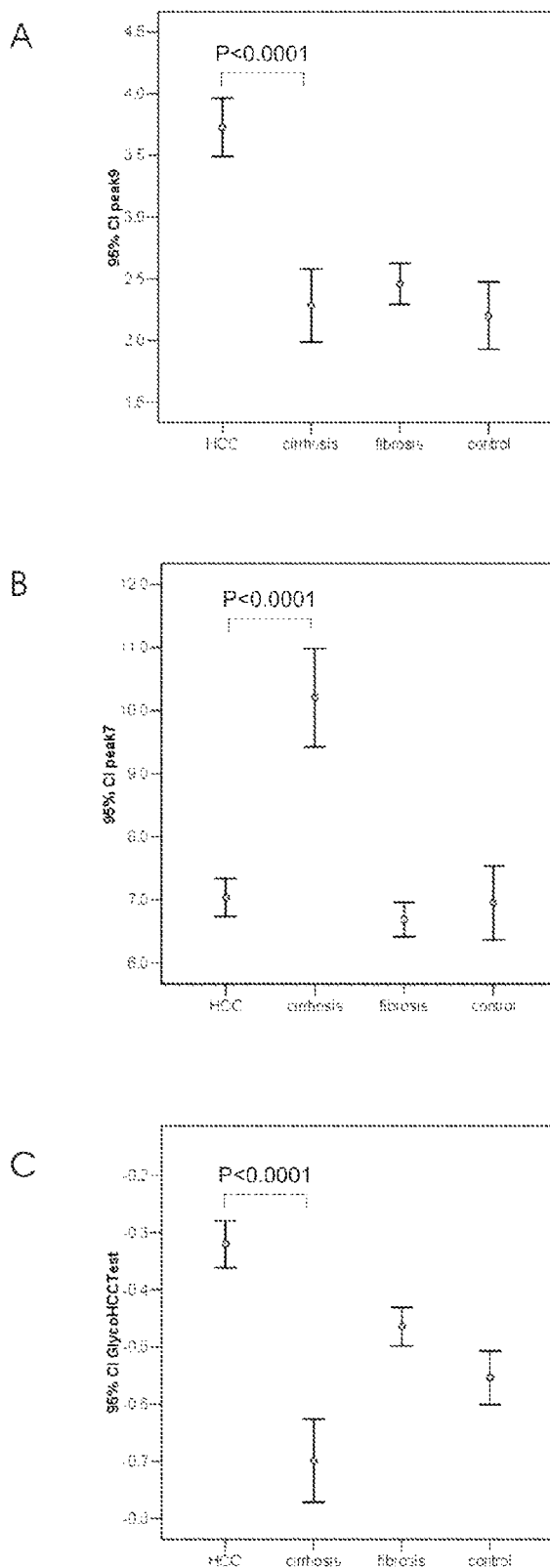
Figure 2:
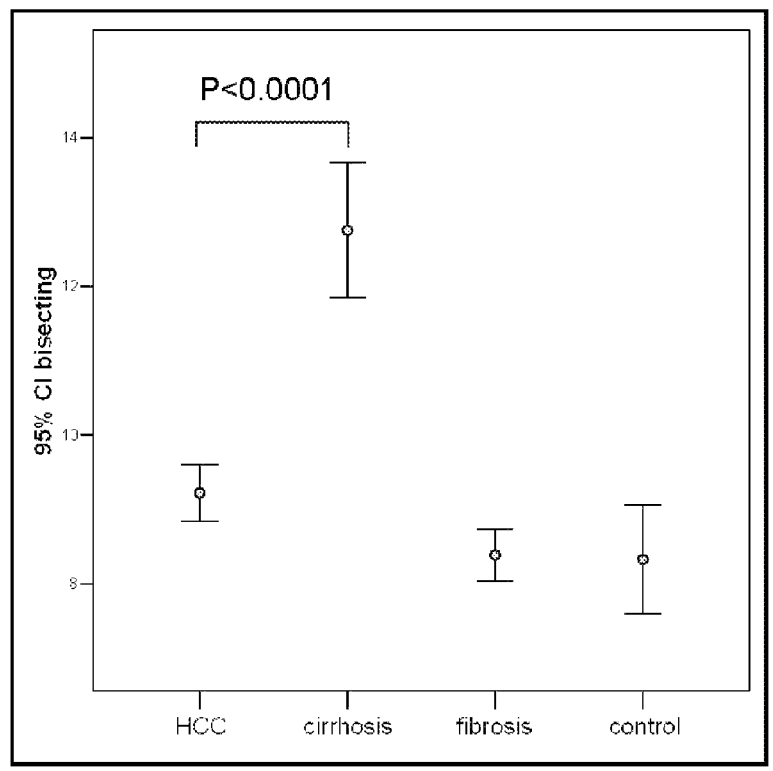
Figure 2:
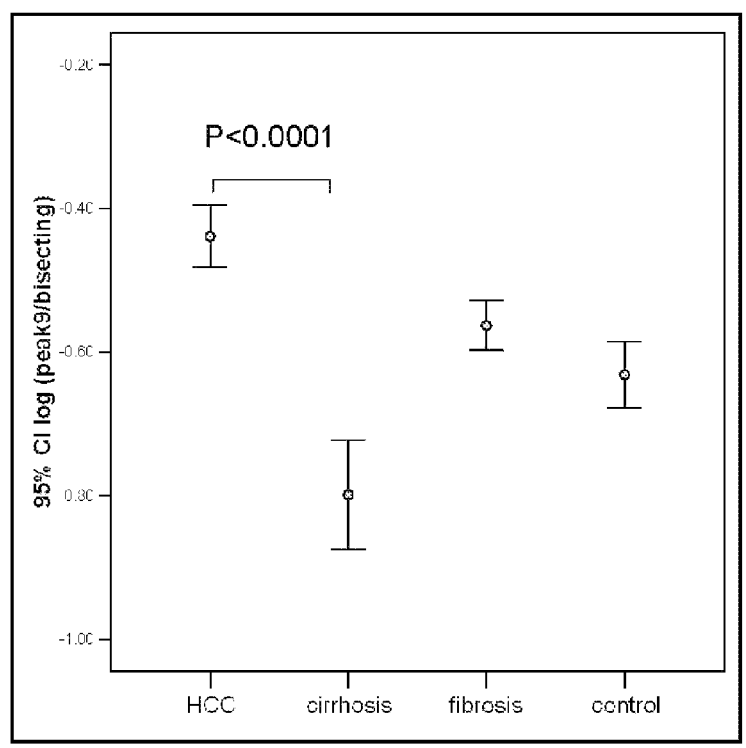

FIG. 2: Trends in derived diagnostic variables for the detection of HCC in cirrhosis patients. The vertical axis represents the glycan values of peak 9, peak 7 and GlycoHCCTest. Glycan value of peak 9 increased in HCC patients (A), whereas peak 7 (B) as well as total bisecting (peak 7+peak 2) (D) increased in cirrhosis patients. GlycoHCCTest was significantly higher in the HCC group than in the cirrhosis, fibrosis and control groups (C). Similarly, the log(peak9/bisecting) was significantly elevated in HCC patients compared to cirrhosis patients (E). Error bars represent 95% confidence interval for the means.

Figure 3:
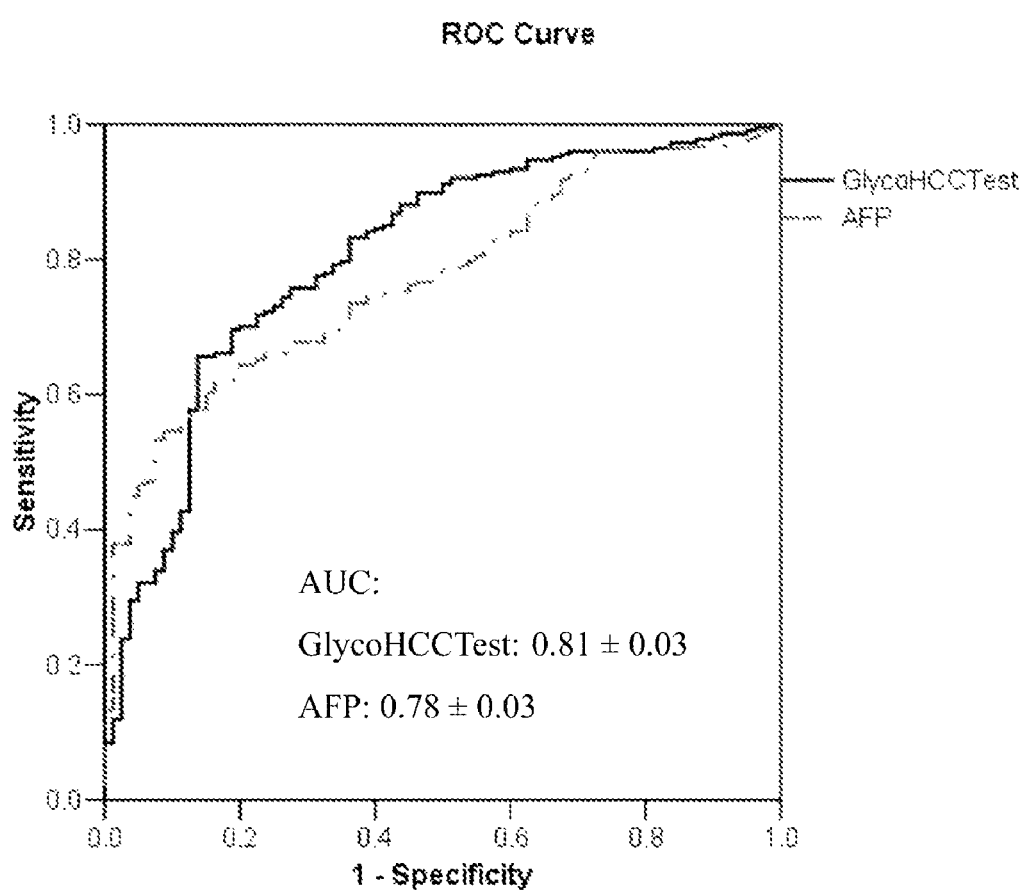

FIG. 3: Receiver operating characteristic (ROC) curve for prediction of clinically significant for detection of HCC in the cirrhosis group using the values of GlycoHCCTest and AFP. Areas under the curves (AUC) show that diagnosis power of GlycoHCCTest (0.81±0.03) resembles AFP (0.78±0.03).

Figure 4:
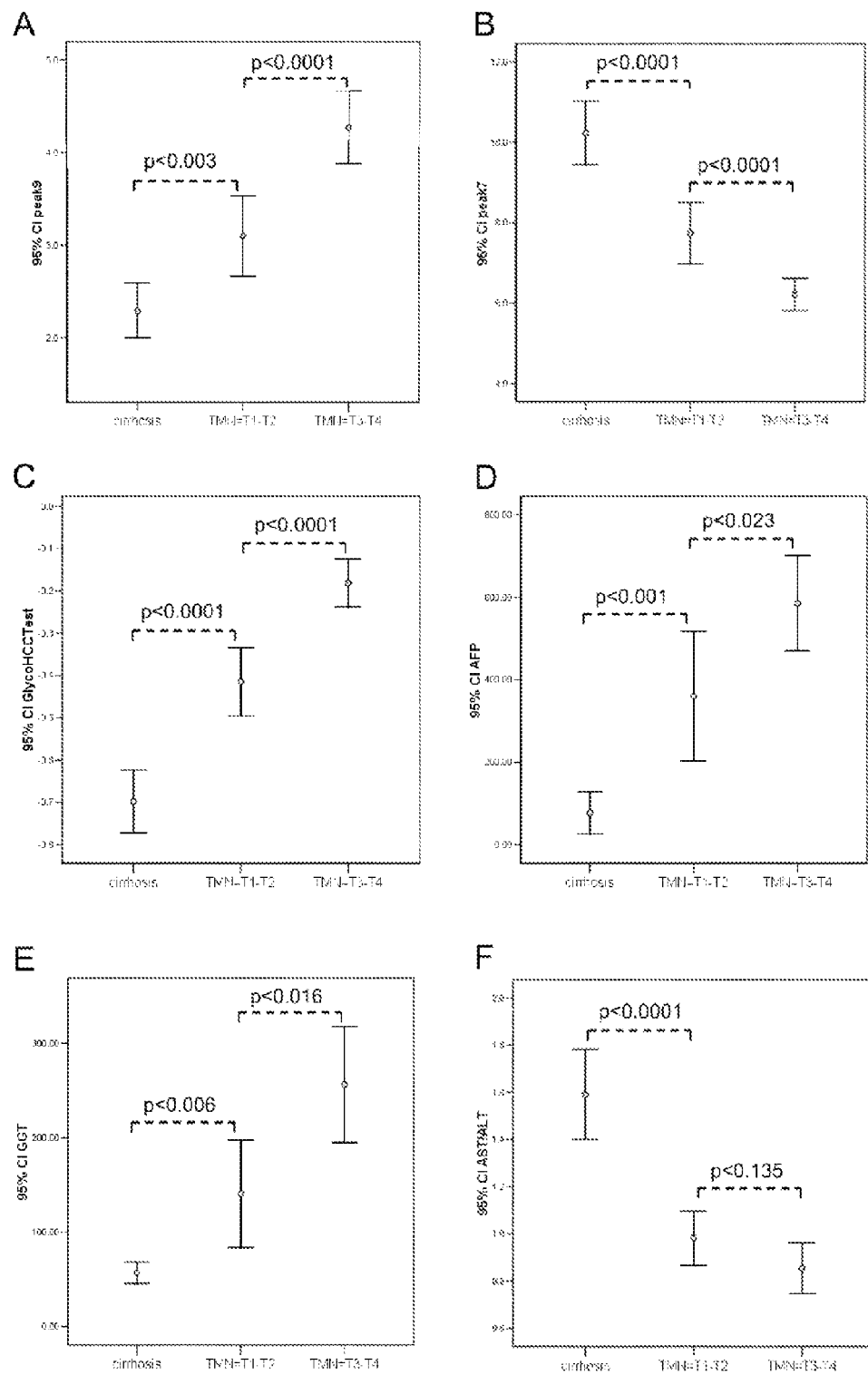

FIG. 4: Relationship between tumor stages and glycan values, AFT, GGT and AST/ALT ratio. Ninety-eight HCC patients with defined tumor stage were analyzed. The levels of peak 9, GlycoHCCTest, AFP and GGT increased significantly in the HCC group compared to the cirrhosis group, whereas peak 7 and the AST/ALT ratio decreased significantly. Peak 9, GlycoHCCTest, AFP and GGT showed a positive association with the tumor stages, whereas peak 7 associated negatively. No correlation of the AST/ALT ratio with tumor stage was found. The vertical axis represents the peak heights of peaks 9 (A) and peak 7 (B), GlycoHCCTest (C), AFP level (D), GGT level (E), and the AST/ALT ratio (F). Error bars represent the 95% confidence interval for the means.

Figure 5:
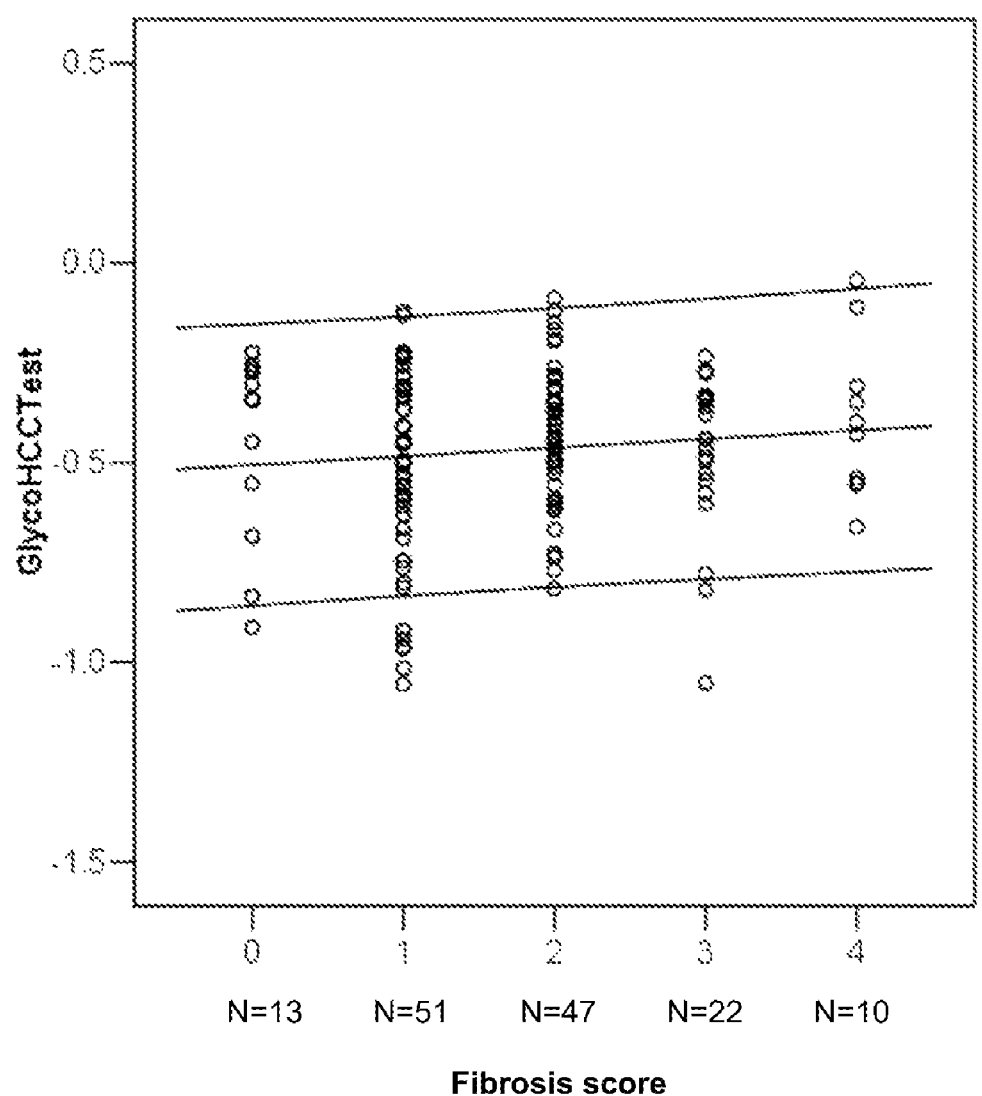

FIG. 5: Correlation of the GlycoHCCTest marker with liver fibrosis. GlycoHCCTest values plotted against fibrosis stages were assessed using the Scheuer scoring system. There was no statistically significant correlation between GlycoHCCTest and fibrosis stages. The upper and lower fit lines represent the 95% confidence interval for the mean values (middle fit line).

Figure 6:
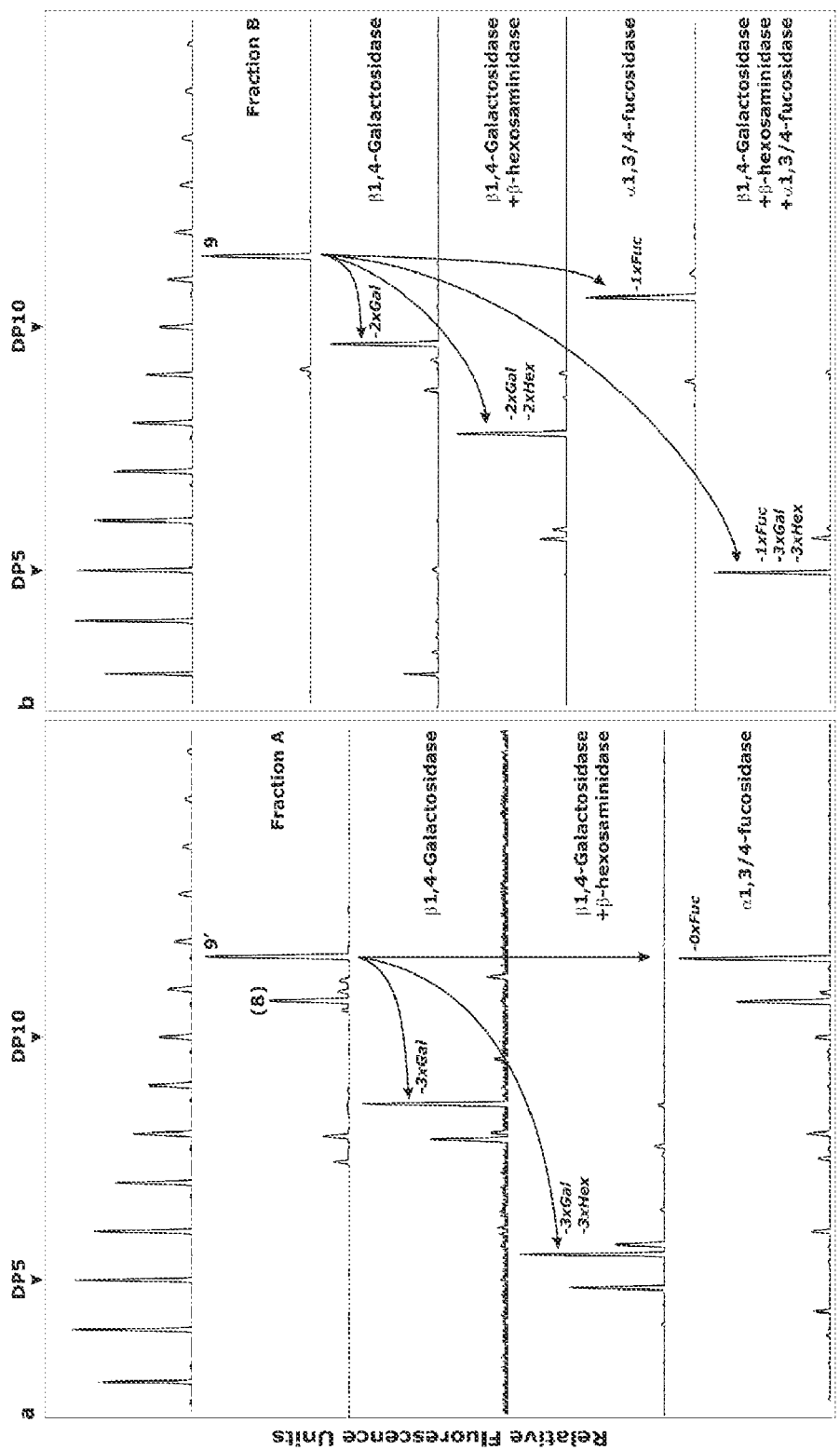

FIG. 6: Exoglycosidase sequencing of peaks 9 FIGS. 6(B) and 9' FIG. 6(A). Total serum N-glycans were separated using NP-HPLC and isolated fractions were treated with single or combined exoglycosidase arrays as indicated. Peaks are numbered as in FIG. 1. gal=galactose; fuc=fucose; hex=N-acetylglucosamine.

Figure 7:
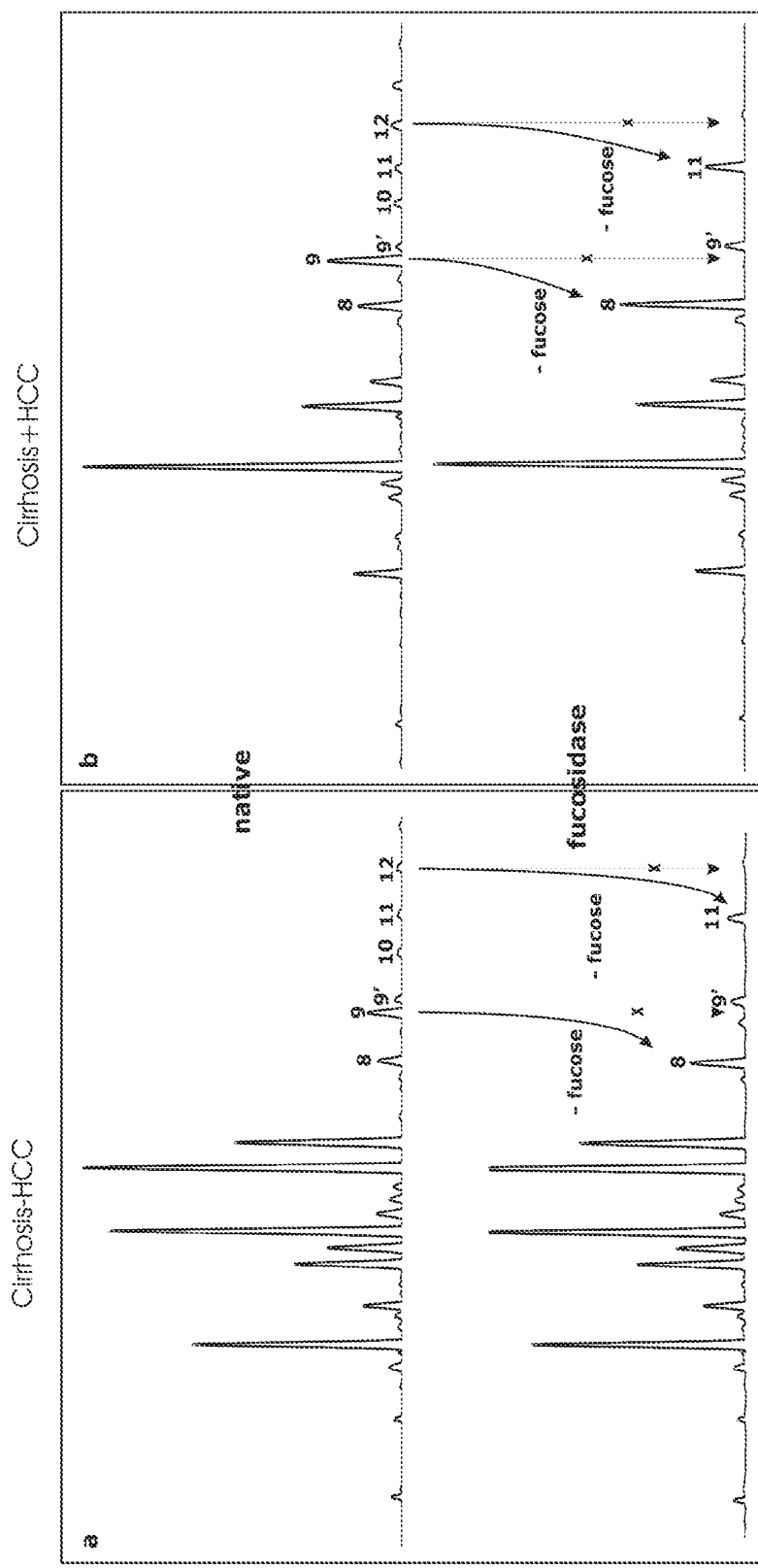

FIG. 7: Exoglycosidase treatment of total serum N-glycans is compared in cirrhosis patients not having HCC (FIG. 7a: Cirrhosis–HCC), with that in cirrhosis patients suffering from HCC (FIG. 7b: Cirrhosis+HCC). Total serum N-glycans were treated with α-1,3/4-fucosidase to show that peaks 9 and 12 are those quantified in the GlycoHCCTest. This enzyme converts these structures into peaks 8 and 11, respectively, whereas their isomeric structures 9' and 12' remain unchanged. Peaks are numbered as in FIG. 1. gal=galactose; fuc=fucose; hex=N-acetylglucosamine.

Figure 8:
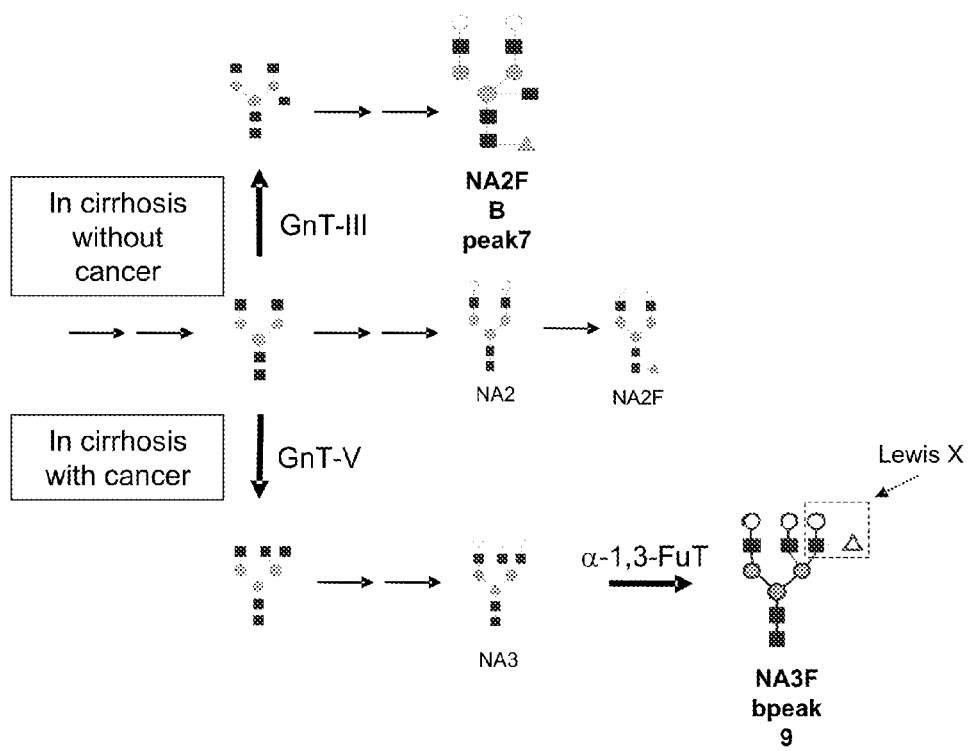

FIG. 8: Scheme of the reactions catalyzed by glycantransferases. The increased concentration of NA3Fb (peak 9) and the decreased level of NA2FB (peak 7) in cirrhosis patients with HCC can be explained by the increased activity of GnT-V competing for the substrate with GnT-III, and resulting in β1-6 branching of N-glycan. This, in turn, leads to enhanced expression of α-1,3-FuT, which produces Lexis X glycan. The consequences of increased expression of GlcNAcT-III are also shown. The dashed box shows an example of a Lewis structure.

Figure 9:
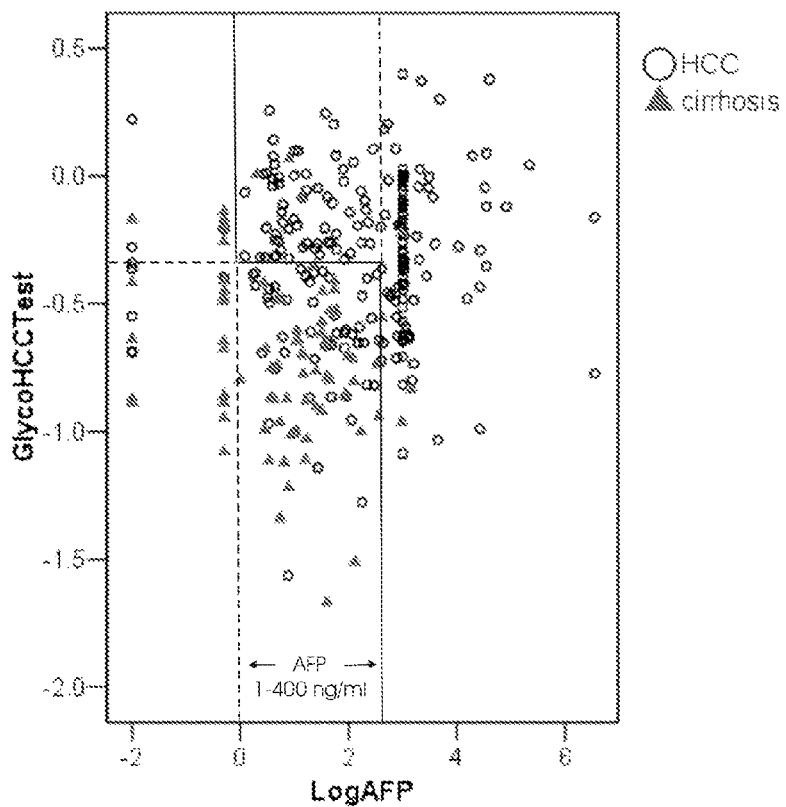

FIG. 9. Relationship between the GlycoHCCTest and LogAFP for diagnosis of HCC in cirrhosis patients. 227 HCC patients plotted against 80 cirrhosis patients were analyzed using GlycoHCCTest plotted against LogAFP. Two vertical lines represent the AFP cutoff lines at 1 ng/ml and 400 ng/ml, and one vertical line represents ROC-determined cutoff value of GlycoHCCTest at −0.34 in the AFP's grey zone (1-400 ng/ml). If AFP was undetectable, we assigned it a value of 0.001 ng/ml.

Figure 10:
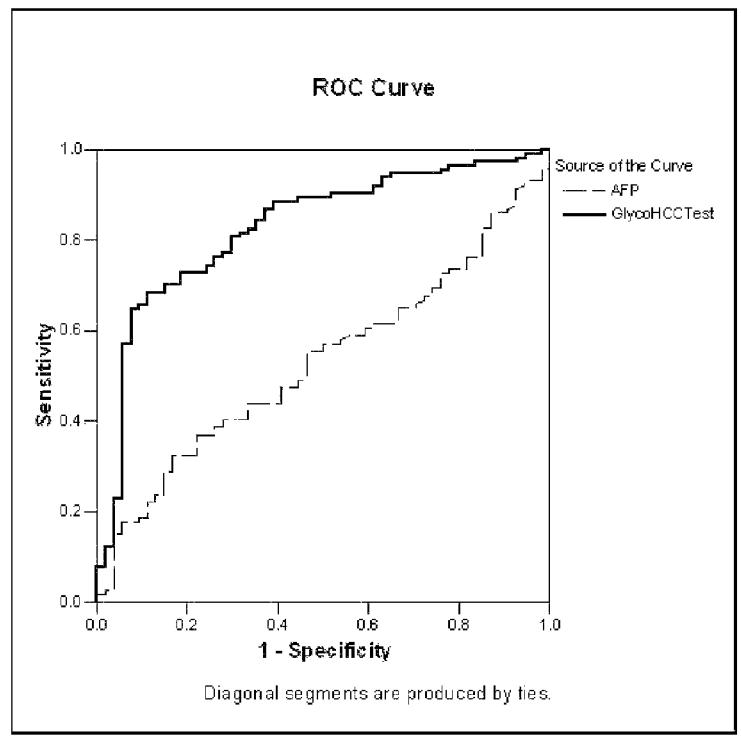
Figure 11:
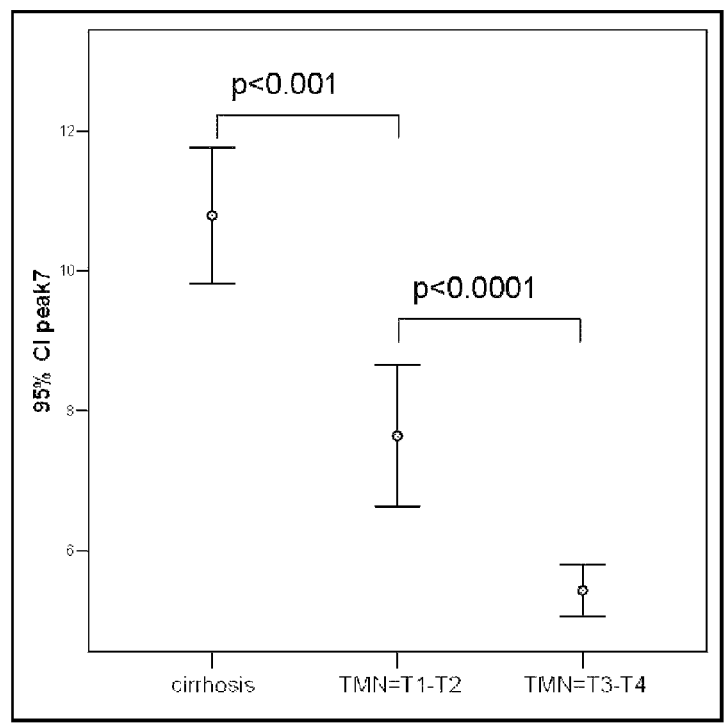
Figure 11:
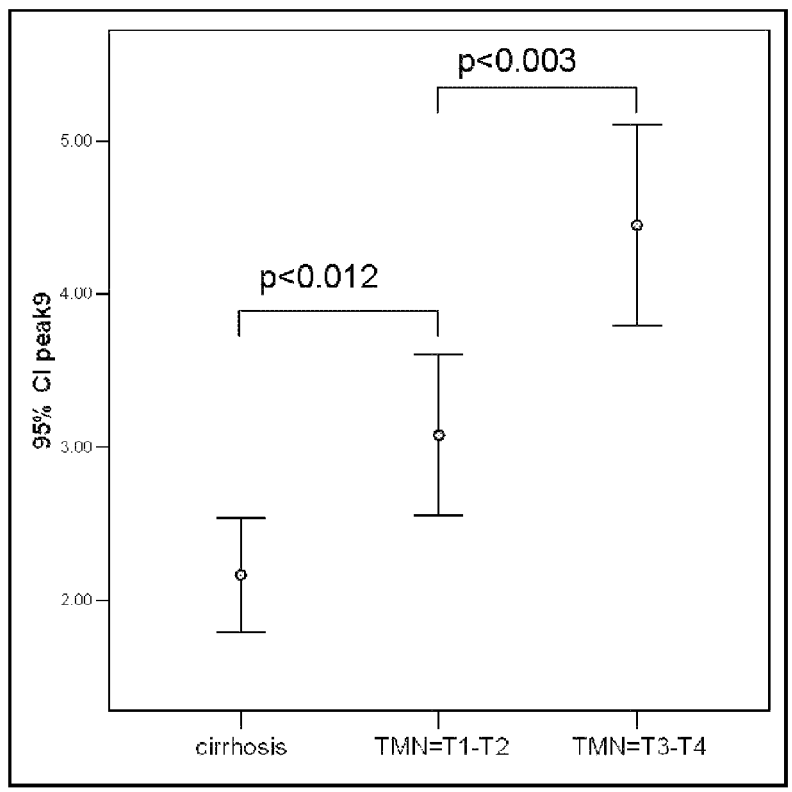
Figure 11:
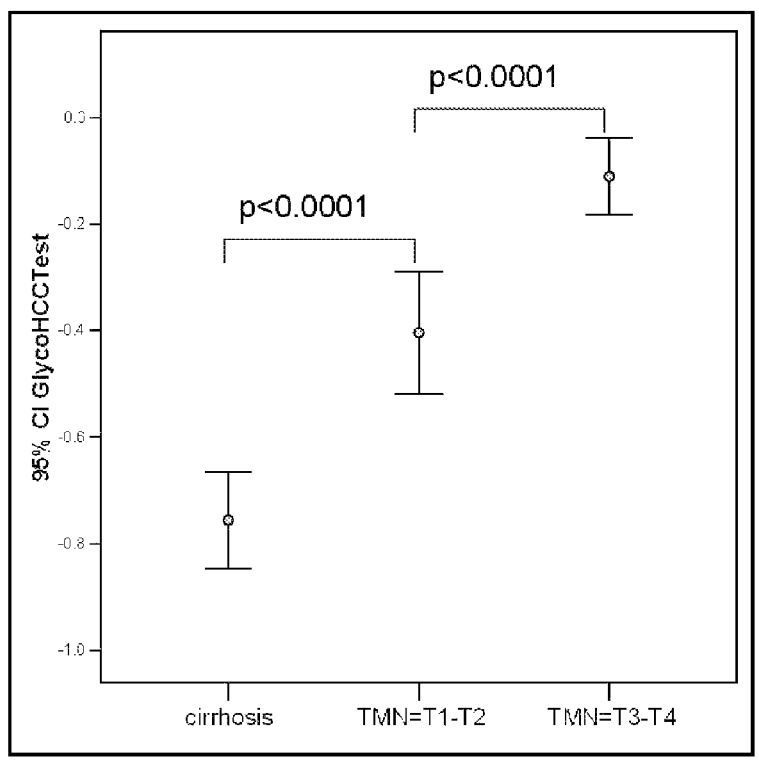
Figure 11:
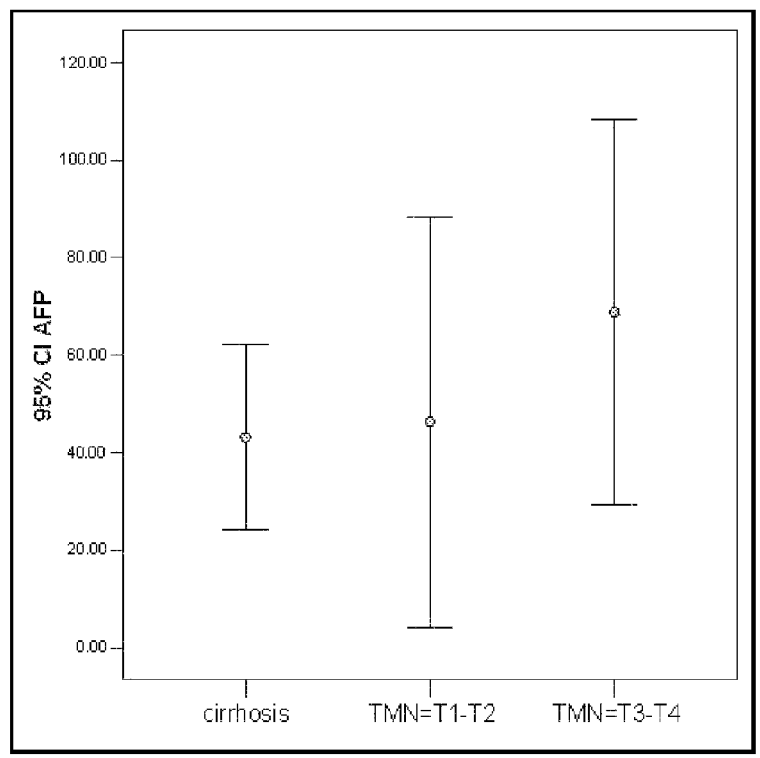
Figure 11:
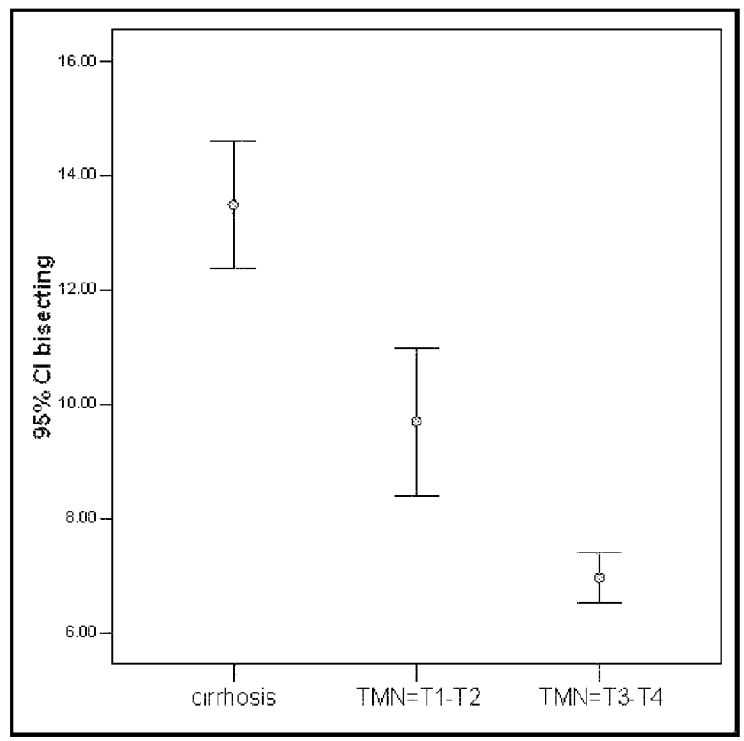
Figure 11:
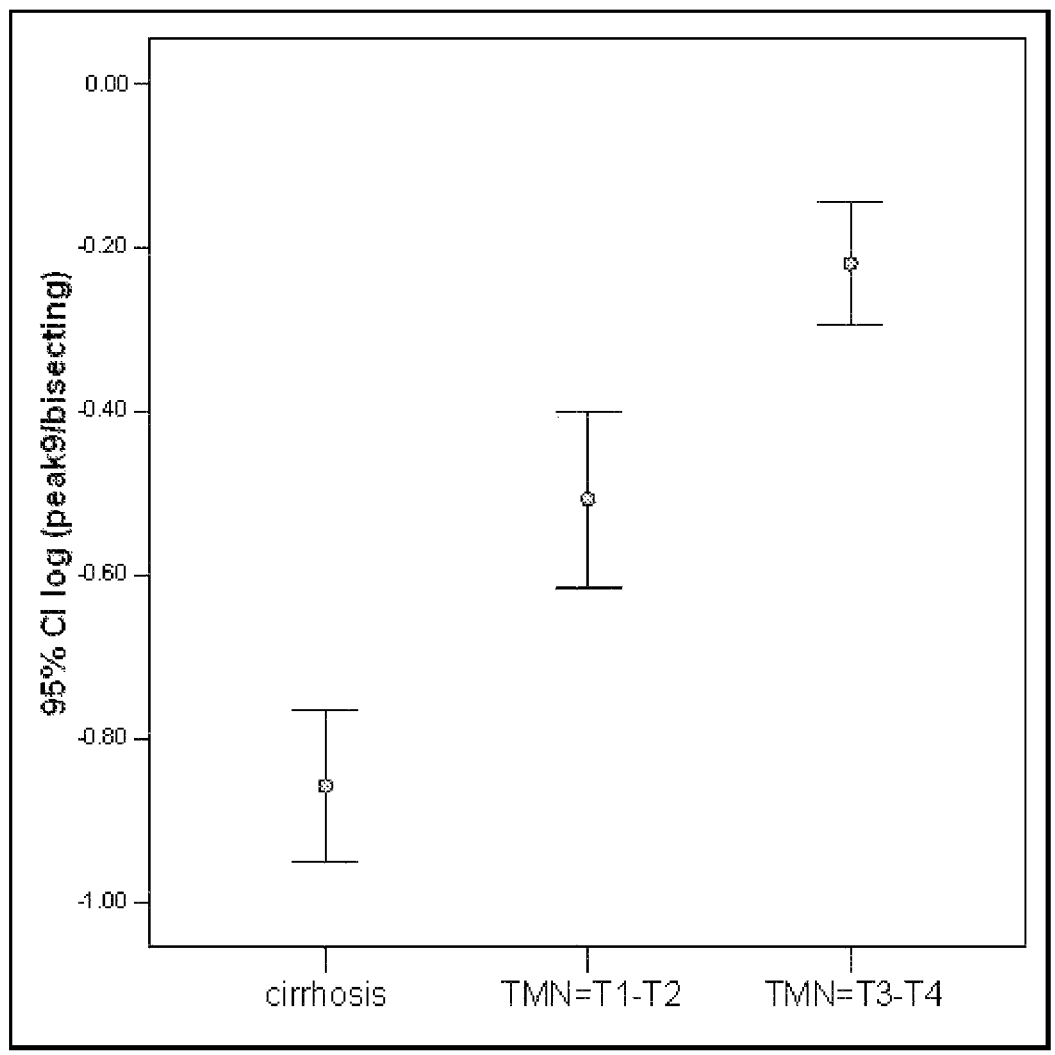

FIG. 10: Receiver operating characteristic (ROC) curve for the prediction of clinically significant for detection of HCC in the AFP grey zone (1~400 ng/ml) using the values of Glyco-HCCTest and AFP. The glycoHCCTest can distinguish HCC patients from cirrhosis patients in the AFP grey zone with an accuracy of 83±3%. The diagnostic power of the glycan marker is much higher than the commonly used AFP marker, which has a lower diagnostic accuracy (53±3%) in the same patient group FIG. 11: Relationship between tumor stages and glycan values combined with AFP. Forty-four HCC patients with defined tumor stage and 54 cirrhosis in the AFP grey zone (1-400 ng/ml) were analyzed. Peak 9 alone and the Glyco-HCCTest showed a positive association with the tumor stages, whereas peak 7 alone associated negatively. No correlation between the AFP-values with tumor stage was found. The vertical axis represents the peak heights of peaks 9 (A) and peak 7 (B), GlycoHCCTest (C), AFP level (D), bisecting GlcNac (peak 2+peak 7) (E) and log ratio of peak 9 and GlcNac bisecting (F). Error bars represent the 95% confidence interval for the means.

AIMS AND DETAILED DESCRIPTION OF THE INVENTION

As liver biopsy is a procedure with significant discomfort to the patient and with some risk for complications, it is not suitable to incorporate it in the routine (generally yearly) follow-up of chronic liver disease patients. Therefore, there is a clinical demand for markers that could routinely assess the progression of the liver disease, and could reliably detect early stage hepatocellular carcinoma. In the present invention we satisfy this need and we have developed a diagnostic able to detect early stage hepatocellular carcinoma. 'Early stage' refers to the T1 or T2 stage of hepatocellular carcinoma (as described further herein in the materials and methods section). In the present invention we have identified a ratio between carbohydrate structures derived from the glycoproteins present in serum and have identified statistically relevant correlations between quantitative parameters derived from these parameters and the histological early hepatocellular carcinoma stage of the patients under study. In other words, amounts of diagnostic carbohydrates or relative amounts between said carbohydrates have surprisingly been identified in the present invention that are correlated with the early stage of hepatocellular carcinoma.

In a first embodiment the invention provides a method of detecting early stage hepatocellular carcinoma or a change in the gradation of hepatocellular carcinoma in a mammal comprising: a) obtaining a sample of serum or blood plasma from the mammal, b) measuring in said sample the ratio between branch alpha (1,3)-fucosylated glycans and bisecting GlcNac core alpha (1,6)-fucosylated glycans and c) attributing said ratio with the presence of early stage hepatocellular carcinoma in said mammal.

In a further embodiment the present invention provides a method of detecting early stage hepatocellular carcinoma or a change in the gradation of hepatocellular carcinoma in a mammal comprising: a) obtaining a sample of serum or blood plasma from the mammal, said sample representing the total mixture of serum or blood N-linked glycoproteins, b) generating a first profile of N-linked carbohydrates or fragments derived there from, or labeled derivatives of said N-linked carbohydrates or said N-linked carbohydrate fragments, or features of said N-linked carbohydrates or said N-linked carbohydrate fragments that are determined by the structure of said N-linked carbohydrates or said N-linked carbohydrate fragments; said N-linked carbohydrates or said N-linked fragments being obtained from the total mixture of serum or plasma proteins present in a serum or plasma sample, wherein said first profile represents the diversity and concentration of N-linked carbohydrate moieties of the total mixture of serum or plasma proteins in said sample, c) measuring in the first profile the ratio of the branch alpha (1,3)-fucosylated glycans and the bisecting GlcNac core alpha (1,6)-fucosylated glycans, d) comparing the measured ratio obtained in step c) with the ratio of said same branch alpha (1,3)-fucosylated glycans and bisecting GlcNac core alpha (1,6)-fucosylated glycans obtained from profiles derived from mammals free of hepatocellular carcinoma in order to detect hepatocellular carcinoma or a change in the gradation of hepatocellular carcinoma, comparing the data obtained in step c) with the ratio in said same mammal in order to detect hepatocellular carcinoma or a change in the gradation of hepatocellular carcinoma, wherein said ratio represents the diversity and concentration of branch alpha (1,3)-fucosylated glycans and bisecting GlcNac core alpha (1,6)-fucosylated glycans of the total mixture of serum or plasma proteins of said mammals, and e) attributing the results of the comparison obtained in step d) to detect hepatocellular carcinoma or a change in the gradation of hepatocellular carcinoma in a mammal.

In another embodiment the ratio between branch alpha (1,3)-fucosylated glycans and bisecting GlcNac core alpha (1,6)-fucosylated biantennary glycans is calculated (measured) from an isolated serum of blood protein. The term 'isolated' means that the calculation of the ratio is not measured on the total amount of serum or blood proteins that are present in a sample but that a particular protein (e.g. an N-glycosylated protein known to be secreted from the liver) is separated (or isolated) from the blood or serum sample. Methods of isolation of proteins (such as antibody-capturing techniques) are well known in the art.

Branch apha (1,3)-fucosylated glycans are shown in FIG. 1 and can be the use of peak 9 or peak 12 or the combination of peaks 9 and 12.

Bisecting GlcNac core alpha-(1,6) fucosylated glycans are shown in FIG. 1 and can be the use of peak 7 or peak 2 or the combination of peaks 7 and 2.

In yet another embodiment the invention provides the use of branch alpha (1,3)-fucosylated glycans and bisecting GlcNac core alpha (1,6)-fucosylated glycans present in blood or serum for the manufacture of a diagnostic assay to detect early stage hepatocellular carcinoma or a change in the gradation of hepatocellular carcinoma.

In yet another embodiment the invention provides the use of branch alpha (1,3)-fucosylated glycans and bisecting GlcNac core alpha (1,6)-fucosylated glycans present in blood or serum in combination with the measurement of the alpha-fetoprotein concentration in serum of blood for the manufacture of a diagnostic assay to detect early stage hepatocellular carcinoma or a change in the gradation of hepatocellular carcinoma.

The wording 'a method to detect liver cancer or hepatocellular carcinoma can be broadly understood as a method for screening, a method for diagnosis or a method for prognosing (or monitoring) liver cancer. The wording 'a change in the gradation of liver cancer or hepatocellular carcinoma' refers to the evolution of liver cancer over time which can mean an improvement of the stage of liver cancer or a stabilization of the stage of liver cancer or a worsening of the stage of liver cancer. A method to detect a gradation of liver cancer is in other words a monitoring instrument which can be used for prognosing a patient (or patient population) previously diagnosed with liver cancer and can be used as a biomarker as an aid for the co-development of a therapeutic for liver cancer. In the wording 'attributing the results of the comparison' refers to the different forms of results that can be obtained. 'Results' can comprise an increase in a value, a decrease in a value, a stability in a value. Alternatively 'results' can fall within a range of values (e.g. 95% confidence interval, a standard deviation) obtained from for example an analysis of groups of patients with a histologically confirmed specific stage of liver cancer. In one embodiment the ratio of the carbohydrates described herein are detected on the N-linked glycoproteins without any isolation step of said carbohydrates; thus the sample can be used as such and does not imply any isolation step of the carbohydrates, whereas the wording 'are isolated from a sample of a body fluid' refers to the fact that the carbohydrates are isolated from the glycoconjugates present in the sample. In a particular embodiment the method of the invention can be used for monitoring the effect of therapy administered to a mammal suffering from liver cancer. In another particular embodiment the method of the invention specifically detects early stage liver cancer. The term 'specifically' refers to the fact that liver cancer can be diagnosed differently from other hepatic disorders comprising liver cirrhosis or even late stage liver cirrhosis or liver fibrosis or still other liver disorders.

The words "glycan" and "carbohydrate" are interchangeable. A 'glycoconjugate' means any compound (e.g. protein or lipid) containing a carbohydrate moiety. The wording 'carbohydrates or fragments derived thereof' means that carbohydrates can be fragmented to yield at least one oligosaccharide or a derivative thereof amongst the products of the fragmentation process. Other products of this fragmentation process might include monosaccharides and oligosaccharides or derivatives thereof. An oligosaccharide is a carbohydrate of which the chemical structure consists of at least two chemically linked units known in the art as monosaccharide. The said fragmentation process can involve enzymatic, chemical and physical treatments. For example, carbohydrates can be treated (or digested) with a glycosidase enzyme (e.g. a sialidase to remove the sialic acid residues from the carbohydrates) and therefore the profile obtained consists of fragments of the carbohydrates. Glycosidase digestions can for example be carried out to obtain a more simple profile of the carbohydrates. Sialic acids may also be removed in a chemical way by mild acid hydrolysis of the carbohydrates. In mass spectrometric analysis methods, the word 'fragments' refers to the fact that carbohydrates are very often fragmented in the process of analysis (for example in collision induced dissociation), in which case the fragmentation products can also yield an oligosaccharide derivative made up of an oligosaccharide chemically linked to the remnant of one or more monosaccharides that were part of the structure of the carbohydrate before fragmentation took place. An example of such an oligosaccharide derivative being the product of a mass spectrometric fragmentation process is known in the art as a cross-ring cleavage product ion. A 'feature of said carbohydrate' refers to any measurable parameter of which the properties and/or the quantity is determined by the structure of the carbohydrate. Examples of such measurable parameters are for example nuclear magnetic resonance parameters such as chemical shifts, homonuclear and heteronuclear coupling constants, Nuclear Overhauser Effects and residual dipolar couplings. Alternatively, such measurable parameters might be the extent of binding to said carbohydrate to other molecules such as lectins and antibodies that recognize specific structural determinants or combinations thereof in the carbohydrate. Yet other such measurable parameters might be the extent of the capacity of the carbohydrate to function as a substrate for an enzyme that specifically modifies certain carbohydrates such as glycosyltransferases and glycosidases.

N-glycans can be released from the glycoproteins in the serum or blood mixture by enzymatic digestion with Peptide N-glycosidase F or other endoglycosidases known in the art. In another embodiment, N-glycans can be released using a procedure involving hydrazine, known to those skilled in the art. In case the profile is obtained on carbohydrates that are still chemically linked to the glycoconjugates in the mixture, one embodiment involves the use of enzymes or chemical procedures to modify the non-glycan part of the glycoconjugate prior to obtaining the profile, such as proteases or enzymes which modify the lipid part of glycolipids. The wording 'a profile of carbohydrates' means any entity comprising qualitative and/or quantitative information on said carbohydrates. For example, this may mean an electrophoretic or chromatographic profile of said carbohydrates. In a particular case the profile is a mass spectrum of said carbohydrates. Alternatively, the profile can be information obtained by Nuclear Magnetic Resonance analysis. In yet another example, the profile can be information describing qualitative or quantitative aspects of lectin binding to the carbohydrates. Alternatively, the profile can be information describing the extent to which the carbohydrates are substrates for specific enzymes such as glycosyltransferases or glycosidases. Such information can include read-outs of measurements of by-products of such enzymatic reactions, such as nucleotides set free in equimolar amounts in glycosyltransferase reactions. In a particular embodiment the wording 'generating a profile of carbohydrates' or 'profiling of carbohydrates' also can imply that the glycan structures are separated and subsequently detected. Usually a number of carbohydrates are identified in a profile of carbohydrates. Usually the carbohydrates are present in a complex mixture and separation is necessary for an efficient detection. Separation can be carried out with methods comprising electrophoretic and chromatographic methods. Detection can be carried out with methods comprising antibody detection, lectin detection, NMR, mass spectrometry and fluorescence. In a particular embodiment it is necessary to chemically and/or enzymatically remove the N-glycans from the glycoproteins before the glycans can be profiled. Methods to prepare N-glycans from glycoproteins are well known in the art. In another particular embodiment it is necessary to derivatize the N-glycans before the separation and the detection. In one approach the method of the present invention for the profiling (includes separation and detection) of N-glycans can be carried out in combination with a DNA-sequencer. However, it is clear for the person skilled in the art that this method can also be applied in connection with capillary electrophoresis systems adaptable to a laser induced fluorescence detector. Such systems for instance include the PACE series Capillary Electrophoresis Systems (Beckman Instruments, Inc., Fullerton, Calif.). The invention can also be applied with any electrophoresis system which is adaptable with a laser induced fluorescence detector. In another embodiment also mass spectrometric detection methods can be used such as MALDI-TOF-MS for the measurement of the amount of at least one carbohydrate or a fragment derived thereof. In mass spectrometric methods very often the carbohydrates are fragmented and therefore in said methods fragments of carbohydrates are detected.

In yet another embodiment the profiling can be carried out with a microfluidics method. Microfluidics is a rapidly growing field and is based on fluid migration through narrow-bore channels created in a solid medium (mostly silica wafers or high-purity glass plates) via techniques borrowed from the microchip industry (photolithography and chemical wet etching). Fluids can migrate through these channels via capillary action or active pumping, and analytes can migrate in fluid-filled channels through electrophoresis (Schmalzing et al (2001) Methods Mol. Biol. 163, 163-173). In yet another embodiment the separation of carbohydrates can be carried out via a chromatographic separation with methods including thin layer chromatography (TLC), high performance liquid chromatography or gas chromatography.

The term "labeled derivatives of said N-linked carbohydrates or said fragments" refers to N-linked carbohydrates that have been labeled with an agent that leads to an efficient detection of the carbohydrates. Said labeled carbohydrates are also called derivatized carbohydrates. As an example, a fluorescing compound can be used for the labelling of the carbohydrates. Said fluorescing compounds are also preferentially charged such that the derivatized compounds can migrate under electrophoretic conditions. When the fluorophore label is uncharged, it can be coupled with a charge imparting species. Said fluorophore label also permits the quantitative measurement of the derivatized carbohydrates by fluorescence. Fluorescing compounds such as 9-aminopyrene-1,4,6-trisulfonic acid (APTS) and 8-aminonaphthalene-1,3,6-trisulfonic acid (ANTS) are particularly suitable for electrophoretic separation of derivatized carbohydrates. Other compounds for fluorescent labelling of carbohydrates include 2-aminopyridine (AP), 5-aminonaphthalene-2-sulfonate (ANA), 1-amino-4-napthalene sulfonic acid (ANSA), 1-amino-6,8-disulphonic acid (ANDA), 3-(4-carboxybenzoyl)-2-quinolinecarboxaldehyde (CBQCA), lucifer yellow, 2-aminoacridone and 4-aminobenzonitrile (ABN).

In a particular embodiment, regarding the detection of the fluorescently labeled carbohydrates, any detection method known in the art can be applied, but preferably the detection is carried out with a laser such as a diode laser, a He/Cd laser or an argon-ion laser. In a particular embodiment, the profile of labeled carbohydrate bands produced by the electrophoretic separation is visualized using an imaging system based on a charge-coupled device (CCD) camera. Information from the CCD camera may subsequently be stored in digital form and analyzed by various computer programs for comparing diagnostic carbohydrate patterns between individuals and between reference standards. In another particular embodiment the gel separated diagnostic carbohydrates may be transferred to an immobilizing membrane, i.e., blotted and then probed with various diagnostic carbohydrate-specific reagents such as lectins or monoclonal or polyclonal antibodies specific for said diagnostic carbohydrates. In a specific embodiment the invention provides a method to detect liver fibrosis in a mammal comprising measuring and detecting at least one glycan structure and/or glycoconjugate that has a different abundance in samples derived from individuals with and without fibrosis by using ligands that specifically bind to said at least one glycan structure and/or glycoconjugate. Ligands comprise lectins and antibodies. For example, the increased abundance of the N-glycan structures (or their conjugates) with a 'bisecting GlcNAc' residue (GnT-III product) in a body fluid sample can be detected with a lectin that specifically recognizes glycans (or their conjugates) that are modified with a bisecting GlcNAc, such as the erythro-agglutinating lectin from *Phaseolus vulgaris* (E-PHA), Annexin V (animal lectin) or mutants thereof with, for example, improved specificity, or antibodies specific for thus modified glycans. Thus, the E-PHA lectin can be used to detect the bisecting GlcNac alpha 1-6 fucosylated glucan structures (also further named glycans (or peak) 2 and 7 in the examples). Alternatively, the increased abundance of the N-glycan structures with a 'bisecting GlcNAc' residue (or their conjugates) can be detected by a reduction in the binding to the N-glycans (or their conjugates) to lectins that only bind N-glycans (or their conjugates) if they are not substituted with a bisecting GlcNAc residue. An example of such a lectin is the lectin from *Canavalia ensiformis* (Con A). The alpha 1-3 fucosylated glycan structure (also designated as glycan (or peak) 9 in the examples) can be detected with the lectin *Lotus A* from *Lotus tetragonolobus* and lectin AAA from *Anguilla Anguilla*. Alternatively the bisecting glycans and alpha 1-3 fucosylated glycans can be immunodetection with antibodies specific for (1,3)-fucose (anti-fucose antibodies) and for bisecting (anti-bisecting antibodies). In the present invention the terms 'bisecting' and 'bisecting GlcNac' are used interchangeably.

In another embodiment the carbohydrate profiling method can be supplemented pre-electrophoretically with one or more internal standards labeled with a chromophore or fluorophore different from the label attached to the carbohydrate analytes. The internal standard allows for accurate and reproducible determination of the electrophoretic mobilities of the derivatized carbohydrate by referencing these mobilities to the mobilities of the components in the internal standard mixture. For example, a rhodamine-labeled oligonucleotide standard Genescan™ 500 (Applied Biosystems, Foster City, Calif., USA) or a mixture of rhodamine-labeled 6-, 18-, 30-, and 42-meric oligonucleotides may be added to the derivatised glycans before profiling. Diagnostics standards may be labeled prior to the labeling of the samples for analysis; however diagnostic standards are preferably labeled concomitantly with the labeling for the standards for analysis. Furthermore, the diagnostic carbohydrates in the standards are preferably quantitated so as to provide for quantitative or qualitative comparisons with the amount of diagnostic carbohydrates in the samples for analysis. Preferred body fluids for analysis are those that are conveniently obtained from patients, particularly preferred body fluids include blood serum and blood plasma.

Although the present invention can be carried out without pre-treatment of the sample prior to the profiling of the (derivatized) glycans, in a particular embodiment, samples for analysis may require processing prior to the separation and quantification of the diagnostic carbohydrates. The precise method of sample processing employed may vary in accordance with a number of factors attributable to the choice of sample fluid and the identity of the diagnostic carbohydrates; these factors include: the abundance of the diagnostic carbohydrate, the concentration of background carbohydrates, the presence of interfering molecules, for example, molecules that adversely affect diagnostic carbohydrate band mobility or the fluorescent labeling of the diagnostic carbohydrates, and whether the fluorescent label has to be separated from the derivatized diagnostic carbohydrates. Suitable methods for this processing or pre-treatment of samples include: dialysis, to remove interfering molecules (e.g. salt for an efficient mass spectrometric detection); ultrafiltration, to concentrate diagnostic carbohydrates and remove interfering molecules; centrifugation, to remove interfering particulates or concentrate cells; precipitation, to remove interfering molecules, removal of albumin from the serum to enrich for glycosylated proteins and hence for lower abundance glycans, deglycosylation with a glycosidase (e.g. a sialidase digest of the glycans) to generate a more simple glycan profile; chromatography such as affinity chromatography to remove for example albumin from the serum In another embodiment of the invention, in order to be able to measure relative amounts of the carbohydrates, diagnostic standards are included on the gels used to analyze the diagnostic carbohydrates in the subject samples; however, the information embodied by the diagnostic standard, e.g., band migration distance and intensity, may also be obtained from comparison with stored records made from diagnostic standards previously subjected to fluorophore assisted carbohydrate electrophoresis under conditions similar to the conditions to which the samples for analysis are exposed. Diagnostic standards may be both positive, i.e., corresponding to the complete carbohydrate pattern in an afflicted individual, or negative, i.e., corresponding to unafflicted individual. Diagnostic standards may have a composition similar to that of samples for analysis in that they may contain both diagnostic carbohydrates and background carbohydrates with composition similar to that found in actual samples. Diagnostic standards may be derived from samples obtained from afflicted and non-afflicted individuals. Alternatively, diagnostic standards may contain one or more diagnostic carbohydrates free of background carbohydrates.

In another embodiment, the invention also includes a diagnostic kit for performing diagnosis of liver cancer or for detecting a change in the gradation of liver cancer. For example a diagnostic kit can be made for performing fluorophore assisted carbohydrate electrophoresis diagnosis of liver cancer. As another example a diagnostic kit can be made for performing mass spectrometric diagnosis of liver cancer. Fluorophore assisted carbohydrate electrophoresis diagnosis kits provide collections of reagents required for performing the diagnosis of liver cancer. Suitable kits enable laboratories to conveniently perform fluorophore assisted carbohydrate electrophoresis diagnosis. Kits may include reagents for performing tests to identify liver cancer. Kits may include diagnostic standards, fluorescent label, blotting and binding materials, e.g., membranes, carbohydrate specific binding reagents, lectins, antibodies, instructions, sample containers, and polyacrylamide gel reagents, precast gels, enzyme buffers, reducing agents (for use in the fluorophore labelling of carbohydrates), and glycosidase enzymes (e.g. sialidase, galactosidase, fucosidase) capable of catalyzing reactions that structurally alter diagnostic carbohydrates. More complete kits may include equipment for performing fluorophore assisted carbohydrate electrophoresis, such as polyacrylamide gel apparatus, CCDs, laser, DNA sequencer, computers, software, and the like. Reagents included in fluorophore assisted carbohydrate electrophoresis diagnosis kits are preferably provided in pre-measured amounts. The kits preferably include the instructions for carrying out the fluorophore assisted carbohydrate electrophoresis method of the present invention.

The diagnostic test is useful in practice because it is sufficiently easy to apply on a large scale by normally trained laboratory staff. Furthermore, since electrophoresis-based high-resolution and high-sensitivity analysers for DNA sequencing and mutation detection are already present in a rapidly increasing number of clinical laboratories or are affordable for most clinical laboratories, the novel diagnostic glycomics test for liver cancer can be run on them. Moreover, the available range of DNA-analysers allows for the sample throughput to be easily scaled from just a few to hundreds of samples per day per machine, depending on the demand of each laboratory. This DNA-analysis equipment offers the added advantage of automation, reducing the complexity of the overall analytical process. Instead of using the total mixture of N-linked glycoproteins the N-glycosylation (id est the two peak profiling of peaks 7 and 9 as described herein) can also be performed studied on purified glycoproteins.

In another embodiment the method for the detection of liver cancer further comprises clinical chemistry parameters and/or histological data. Thus, the present invention can also be conveniently carried out in combination with clinical chemistry parameters and/or histology and/or imaging parameters. Measurement of clinical chemistry parameters comprises measurement of levels of bilirubin and/or albumin and/or prothrombin time and/or C-reactive protein and/or IgA abundance and/or serum hyaluronic acid concentration and/or aminotransferases and/or the several liver metabolism test known in the art. In a preferred embodiment the glycoHCCtest of the present invention is combined with the measurement of alpha-fetoprotein. Histology comprises liver biopsies. Imaging comprises ultrasound and/or CT-scan and/or MRI-scan and/or imaging of radioactive tracers specific for the liver.

The examples which follow are offered as descriptive of certain embodiments. As such they are exemplary only and are not limiting in their nature.

EXAMPLES

1. Altered N-glycan Profiles in HCC and Cirrhosis Patients

Using DSA-FACE, we examined the N-glycome profile from desialylated sera (FIG. 1) of Chinese patients with liver fibrosis (n=143) and liver cirrhosis with or without HCC complication (HCC n=227; cirrhosis n=80). We also analyzed the blood from healthy donors (n=130). We quantified each peak by normalizing its height to the sum of the heights of all peaks in the profile, and then statistically compared the peaks of healthy controls, fibrosis patients, cirrhosis patients and HCC patients. To enable specific HCC detection on a cirrhosis background, we focused on identifying glycan structures whose abundance would not increase in cirrhosis patients, but would be elevated in HCC patients. We found one peak with this pattern, namely Peak 9 (FIG. 2A). The abundance of this peak was strongly associated with HCC (P<0.0001), potentially indicating a common mechanism in its up-regulation. Moreover, peak 7 and total bisecting (peak 7+peak 2) were significantly lower in HCC patients than in cirrhosis patients (p<0.0001) (FIGS. 2B and 2D). The log (peak9/peak7) ratio and the log(peak9/bisecting) were significantly elevated in HCC patients (p<0.0001) compared to cirrhosis patients, fibrosis patients and healthy controls (FIGS. 2C and 2E). Ultimately, we renamed log(peak9/peak7) as GlycoHCCTest, in parallel to the "GlycoCirrhoTest" nomenclature we adopted in our previous study, in which we used the same method but defined a different set of peaks (19).

2. The Glycan Marker has the Same Efficacy of HCC Diagnosis as AFP

Though measurement of serum AFP is important in screening for HCC, previous studies (15) have indicated that it is of limited utility in detecting HCC in liver cirrhosis patients due to frequent mild elevation of AFP levels in cirrhosis. The low specificity of AFP for HCC at low thresholds was also found in our cirrhotic patient population, as can be seen in Table 2, which presents data for different AFP cutoff values.

As determined by ROC curve analysis, the glycoHCCTest could distinguish HCC patients from cirrhosis patients with an accuracy of 81±3% (FIG. 3). The diagnostic accuracy of the glycan marker is very similar to the commonly used AFP marker, which had a diagnostic accuracy of 78±3% in the same patient group (FIG. 3). Moreover, the GlycoHCCTest at cutoff value −0.34 detected HCC with the 88% specificity and 57% sensitivity, which resembles those of AFP at cutoff 100 ng (Table 2).

3. Glycan Alterations are Associated with Tumor Stage

To evaluate the correlation between the HCC glycomic marker and tumor stage, a HCC subgroup (n=98) with defined tumor size and stages was analyzed for glycomics changes. According to the TNM criteria, the HCC patients were classified as T1 (n=6), T2 (n=28), T3 (n=59) and T4 (n=5). Since only a few patients were classified as T1 or T4, for the purpose of statistical analysis we combined T1 with T2 as one group, and T3 with T4 as another. The concentration of peak 9 was higher in the T3-T4 group than in the T1-T2 group (FIG. 4A), whereas a negative correlation of peak 7 with tumor stage was revealed (FIG. 4B). The GlycoHCCTest was positively associated with tumor stage (p<0.0001) (FIG. 4C).

The AST/ALT ratio has been considered a sensitive marker of cirrhosis progression in viral hepatitis (24). γ-glutamyl-transferase (GGT) has also shown good sensitivity when viral hepatitis reaches the stage of causing structural damage (25). We therefore analyzed the correlation of tumor stage with AFP, GGT and the AST/ALT ratio in this subset HCC patients. As shown in FIG. 4D-E, the levels of AFP and GGT were higher in the HCC group than in the cirrhosis group (p<0.001 and 0.006, respectively) and they were positively associated with tumor stage (p<0.023 and p<0.016, respectively). The AST/ALT ratio is significantly lower in HCC patients than in cirrhosis patients (p<0.0001), and its correlation with tumor stage is not significant (p<0.174) (FIG. 4F). Pearson correlation showed that the level of GlycoHCCTest has no correlation with the level of AFP (p=0.5680) and AST/ALT ratio (0.351), but is associated with the GGT concentration (p=0.001). GGT is also called cholestatic liver enzyme. Because obesity, heavy drinking, fatty liver, and certain medications or herbs that are toxic to the liver can elevate GGT levels, it cannot be excluded that the high level of GlycoHCCTest present in HCC patients is not associated with cholestasis. In addition, we evaluated the HCC glycomics marker in a group of patients with chronic HBV infection (n=143). The GlycoHCCTest value was consistently constant among the fibrosis stages in fibrosis patients, indicating that it is HCC-specific (FIG. 5).

4. Structural Analysis of the Glycans Allowing HCC Diagnosis in Cirrhosis Patients The N-glycan structures were verified by exoglycosidase sequencing on NP-HPLC-purified fractions. Here, we give an example for peaks 9 and 9' (FIG. 6). From the major structure in fraction A (peak 9') (FIG. 6a), three galactoses can be removed using a β-1,4-galactosidase. When this enzyme is combined with an N-acetylhexosaminidase, three extra N-acetylglucosamine residues are taken off. This indicates an N-glycan with three unmodified, fully galactosylated branches. Moreover, this structure is fucosylated, as it is sensitive to the low-specificity alpha-fucosidase (not shown). This structure is not a substrate for the alpha-1,3/4-fucosidase, indicating that this fucose modification is alpha-1,6-bound to the core N-acetylglucosamine. When the structure in fraction B (peak 9) (FIG. 6b) is treated with the galactosidase, only two residues are removed. An additional hexosaminidase digestion removes two other residues, indicating that one of the three branches is modified, so that it is insensitive to the enzymatic activity. This was confirmed by its sensitivity to the alpha-1,3/4-fucosidase, which can remove a fucose only when it is bound to a branch N-acetylglucosamine residue. When all three enzymes are combined, an extra galactose and an N-acetylglucosamine are removed after the fucosidase removes the hindering fucose. Overall, these experiments show that peaks 9 and 9' are isomers, differing only in the position of a fucose residue.

To ensure that the GlycoHCCTest quantifies peak 9 and not its isomers, we performed an α-1,3/4-fucosidase digestion on total serum (FIG. 7). This enzyme transforms peaks 9 and 12 into peaks 8 and 11, respectively; peaks 9' and 12' remain unaltered.

5. Enhancing Accuracy of HCC Diagnosis by Combining GlycoHCCTest with AFP

Though measurement of serum AFP is important in screening for HCC, previous studies (18) have indicated that it is of limited use in detecting HCC in liver cirrhosis patients due to frequent mild elevation of AFP levels in cirrhosis. In practice, therefore, one has to use a much higher cutoff value for AFP (400 ng/ml instead of 10 or 20 ng/ml, which can be used in non-cirrhotic patients) to maintain high specificity, with concomitant reduction in the sensitivity of HCC detection. The low specificity of AFP for HCC at low thresholds was also found in our cirrhotic patient population, as can be seen in Table 2, which presents data for different AFP cutoff values. The cutoff AFP<1 ng/ml had high sensitivity, up to 96% for HCC detection, but its specificity was low (26%). However, the specificity for diagnosing HCC increased up to 95% at a cutoff value for AFP of 400 ng/ml, and the sensitivity dropped to 46%. Thus, it is necessary to have complementary marker (s) to detect HCC when AFP level is less than 400 ng/ml. To evaluate whether the GlycoHCCTest can help in resolving this issue, we plotted GlycoHCCTest against LogAFP (FIG. 9). We noticed that at the low level of AFP (<1 ng/ml), there were only 3% true HCC cases (9/227) and 26% cirrhosis cases (21 of 80) as shown in FIG. 9. In order to increase the specificity of detecting HCC, we applied our GlycoHCCtest in the patients with AFP>1 ng/ml and AFP<400 ng/ml (AFP's 'grey zone', which encompassed 114 of 227 HCC patients and 55 of 89 cirrhosis patients). The GlycoHCCTest (at cutoff value −0.34) detected HCC in this AFP's grey zone with 95% specificity (3/55 false positive) and 57% sensitivity (65/114 true positive) (Table 3; FIG. 9). As determined by ROC curve analysis (FIG. 10), the glycoHCCTest could distinguish HCC patients from cirrhosis patients in the AFP grey zone with an accuracy of 83±3%. The diagnostic power of the glycan marker is much higher than the commonly used AFP marker, which had a lower diagnostic accuracy (53±4%) in the same patient group (FIG. 10). This made it clear that the GlycoHC-CTest could be used for HCC patients within AFP values of 1-400 ng/ml. Consequently, by combining AFP>400 ng/ml with GlycoHCCTest cutoff>−0.34 in the AFP's grey zone, we could distinguish HCC from cirrhosis with 74% sensitivity and 91% specificity (Table 3). In other words, combining GlycoHCCTest with AFP in diagnosis of HCC increases the sensitivity by 28% compared to AFP alone (cutoff>400 ng/ml; 46% sensitivity).

6. The Combination of the GlycoHCC-Test with AFP (Grey Zone) are Positively Associated with HCC Tumor Staging To evaluate the correlation between the HCC glycomic marker and tumor stage in the AFP grey zone, a HCC subgroup (n=44) with defined tumor size and stages falling in the AFP grey zone (1-400 ng/ml) was analyzed for changes in the glycosylation profile. According to the TNM criteria, the HCC patients were classified as T1 (n=3), T2 (n=15), T3 (n=25) and T4 (n=1). A cirrhosis (n=55) group with the AFP level 1-400 ng/ml was used as comparative reference. The concentration of peak 9 was higher in the T3-T4 group than in the T1-T2 group (FIG. 11A), whereas a negative correlation of peak 7 and bisecting (peak 2+peak 7) with tumor stage was revealed (FIGS. 11B and E). The GlycoHCCTest was significantly positively associated with tumor stage (p<0.0001) (FIG. 11C). Also the log ratio of peak 9/bisecting glycans (FIG. 11F) were significantly associated with the tumor stage. However, the AFP value has no correlation with tumor stage within the grey zone (FIG. 11D).

The cutoff values of GlycoHCCTest in diagnosis of HCC in the AFP gray zone with the specificity and sensitivity is shown in the Table 4. The glycoHCCTest showed diagnosis power for detection of HCC in AFP gray zone with a variation in the sensitivity between 68.2 to 88.6% and specificity between 81.1 to 94.3%.

Materials and Methods
Patients Selection

The study was approved by the Ethics Committee of Peking University Health Science Centre, and by the Ethics Committee of Renji Hospital, Shanghai Second Medical University. Informed consent was obtained from each patient.

Patients were recruited from four hospitals in Beijing, China (Youan hospital, Wujing hospital, Ditan hospital and Beida hospital), Nanjing 2$^{nd}$ Hospital in Nanjing, China, and Shanghai hospital, China. In total, 497 HBV-infected patients with chronic liver diseases were recruited; 47 were excluded due to metastasis, autoimmune liver disease, drug-related hepatitis, alcoholic hepatitis or obstructive jaundice. All patients were negative for antibodies against HAV, HCV and HDV (Abbott EIA), EBV and CMV (EIA, Human Co. Ltd, Germany), and HEV (EIA, Genelabs, Singapore).

Laboratory Tests

The main clinical and biological data of the patients are summarized in Table 1. All patients had either fibrosis or cirrhosis, and were infected with hepatitis B virus (HBV), diagnosed by serological detection of HBsAg, anti-HBsAg (HBsAb), HBeAg, anti-HBeAg (HbeAb), anti-HBcAg (HB-cAb) and HBV DNA. The extent of liver damage was assessed by measurement of alanine aminotransferase (ALT), aspartate aminotransferase (AST), total bilirubin, albumin, total serum protein, and γ-glutamyltransferase (GGT).

Clinical Stage and Tumor Stage

The diagnosis of liver fibrosis and cirrhosis were made by histological examination, the imaging procedures and several liver function tests. Fibrosis stage was determined using Scheuer's classification. Liver samples were evaluated independently by two experienced hepatopathologists who were unaware of the glycomics results. The liver fibrosis patients (n=143) had been extensively studied and their clinical data had been published previously by Min-De Zeng et al. (21). Liver cirrhosis patients were staged according to the Child-Pugh classification. Cirrhosis patients with HCC (n=227) were diagnosed histologically by biopsy, autopsy and surgical specimens, and clinically by ultrasonography and/or computed tomographic scanning on a regular examination, and combined with measurement of AFP (cutoff 20 ng/ml). The tumor stages were ranked according to the TNM criteria (22): T1=solitary without vascular invasion; T2=solitary with vascular invasion, Multiple ≦5 cm; T3=Multiple >5 cm, invading major branch of portal or hepatic veins; T4=invading adjacent organs other than gallbladder perforates visceral peritoneum. All blood samples were drawn before any treatment or operation. Blood from a reference group of 130 healthy individuals, in whom HCC was excluded by ultrasound, were obtained from Beijing and Shanghai Red Cross Centers.

Processing Blood Samples for Protein N-Glycome Analysis

The N-glycans present on the proteins in 2 μl of serum were released, labeled, and analyzed as described previously (39, 23). Labeled N-glycans were analyzed by DNA Sequencer Assisted-Fluorophore Assisted Carbohydrate Electrophoresis (DSA-FACE) technology, using a capillary electrophoresis (CE)-based ABI3130 sequencer. Data were analyzed using the GeneMapper v3.7 software (Applied Biosystems, Foster city, CA). We measured the heights of the peaks that were detected in all the samples to obtain a numerical description of the profiles, and analyzed these data with SPSS 12.0 statistical software.

Structural Characterization

For structural analysis of APTS-labeled serum N-glycans, they were first separated by normal phase HPLC as described (23). Appropriate amounts were then digested with exoglycosidase as described above, using the following enzymes: *Streptococcus pneumonia* β-1,4-galactosidase (0.4 mU/digest), Jack Bean β-N-acetylhexosaminidase (10 mU/digest), Bovine kidney α-fucosidase (2 mU/digest) and Almond meal α-1,3/4-fucosidase (1 μU/digest) (all from Prozyme, San Leandro, Calif.). DSA-FACE was used to analyze the digestion products.

Statistical Analysis

Statistical analyses were performed with SPSS for Windows software (SPSS, Chicago, Ill., USA). Results are presented as means±SD. All reported P-values are two-tailed, using a t-test for independent samples. Pearson coefficients of correlation (with 95% confidence intervals and their associated probability (p) were used to evaluate the relationship between parameters. The Receiver Operating Characteristics (ROC) curve was used as an index of accuracy; values close to 1.0 indicating high diagnostic accuracy.

Tables:

TABLE 1

Characteristics of Chinese HCC and cirrhosis patients with HBV infection

| case group | Cirrhosis + HCC | Cirrhosis − HCC |
|---|---|---|
| case number | 227 | 80 |
| male number (%) | 201 (88.5%) | 54 (67.5%) |
| age (year) | 53.2 ± 10.4 | 50.2 ± 11.5 |
| HBV DNA (copy) | 4.4E+06 ± 1.9E+07 | 3.6E+07 ± 1.0E+08 |
| HBsAg+ (%) | 87.5 | 95 |
| HBeAg+ (%) | 30.5 | 41.3 |
| HBeAb+ (%) | 50.8 | 42.5 |
| HBcAb+ (%) | 92.2 | 95 |
| AST (IU/L) | 104.5 ± 208.3 | 100.7 ± 173.5 |
| ALT (IU/L) | 74.5 ± 90.4 | 92.7 ± 159.5 |
| GGT (IU/L) | 172.2 ± 189.7 | 58.1 ± 45.4 |
| Albumin (g/L) | 36.8 ± 6.6 | 33.9 ± 8.2 |
| total bilirubin (umol/L) | 44.4 ± 99.9 | 32.0 ± 36.0 |
| total serum protein (g/L) | 59.0 ± 22.4 | 44.7 ± 18.9 |
| AFP (ng/ml) | 34331.2 ± 331192.9 | 75.9 ± 227.8 |
| Decompensated liver cirrhosis (%) | 37 (16.3%) | 56 (70%) |

TABLE 2

Diagnostic values of AFP for the detection of HCC

| AFP cut-off (ng/ml) | HCC (n) | false-positive (n) | sensitivity % | specificity % |
|---|---|---|---|---|
| 1 | 218 | 59 | 96 | 26 |
| 10 | 174 | 40 | 77 | 50 |
| 20 | 162 | 29 | 71 | 64 |
| 100 | 129 | 10 | 57 | 88 |
| 200 | 115 | 6 | 51 | 93 |
| 400 | 104 | 4 | 46 | 95 | n: case number

TABLE 3

Diagnostic values of GlycoHCCTest combination with AFP for detection of HCC

| GlycoHCCTest cutoff >−0.34 | HCC (n) | false-positive (n) | sensitivity % | specificity % |
|---|---|---|---|---|
| in AFP grey zone: 1~<400 ng/ml | 65 | 3 | 57 | 95 |
| in AFP grey zone combination with AFP >=400 ng/ml | 169 | 7 | 74 | 91 |

TABLE 4

Diagnosis power of GlycoHCCTest for detection of HCC in the AFP grey zone (1~400 ng/ml)

| | total HCC | HCC = T1 | HCC = T2 | HCC = T3 | HCC = T4 | false positive | sensitivity % | specificity % |
|---|---|---|---|---|---|---|---|---|
| GlycoHCCTest | 44 | 3 | 15 | 25 | 1 | 55 | | |
| cutoff > −0.34 | 30 | 3 | 4 | 23 | 0 | 3 | 68.2 | 94.3 |
| cutoff > −0.40 | 34 | 3 | 7 | 24 | 0 | 4 | 77.3 | 92.5 |
| cutoff > −0.45 | 36 | 3 | 8 | 25 | 0 | 7 | 81.8 | 86.8 |
| cutoff > −0.50 | 39 | 3 | 10 | 25 | 1 | 10 | 88.6 | 81.1 |

REFERENCES

1. Bruix J, Boix L, Sala M, Llovet J M. Focus on hepatocellular carcinoma. Cancer Cell 2004; 5:215-219.
2. Liaw Y F. Prevention and surveillance of hepatitis B virus-related hepatocellular carcinoma. Semin Liver Dis 2005; 25 Suppl 1:40-47.
3. Koike K. Molecular basis of hepatitis C virus-associated hepatocarcinogenesis: lessons from animal model studies. Clin Gastroenterol Hepatol 2005; 3:S132-135.
4. Bosch F X, Ribes J, Borras J. Epidemiology of primary liver cancer. Semin Liver Dis 1999; 19:271-285.
5. Caturelli E, Bartolucci F, Biasini E, Vigliotti M L, Andriulli A, Siena D A, Attino V, et al. Diagnosis of liver nodules observed in chronic liver disease patients during ultrasound screening for early detection of hepatocellular carcinoma. Am J Gastroenterol 2002; 97:397-405.
6. Bolondi L. Screening for hepatocellular carcinoma in cirrhosis. J Hepatol 2003; 39:1076-1084.
7. Yuen M F, Lai C L. Serological markers of liver cancer. Best Pract Res Clin Gastroenterol 2005; 19:91-99.
8. Zhou L, Liu J, Luo F. Serum tumor markers for detection of hepatocellular carcinoma. World J Gastroenterol 2006; 12:1175-1181.
9. el-Houseini M E, Mohammed M S, Elshemey W M, Hussein T D, Desouky O S, Elsayed A A. Enhanced detection of hepatocellular carcinoma. Cancer Control 2005; 12:248-253.
10. Qin L X, Tang Z Y. Recent progress in predictive biomarkers for metastatic recurrence of human hepatocellular carcinoma: a review of the literature. J Cancer Res Clin Oncol 2004; 130:497-513.
11. Nguyen M H, Keeffe E B. Screening for hepatocellular carcinoma. J Clin Gastroenterol 2002; 35:S86-91.
12. El-Aneed A, Banoub J. Proteomics in the diagnosis of hepatocellular carcinoma: focus on high risk hepatitis B and C patients. Anticancer Res 2006; 26:3293-3300.
13. Daniele B, Bencivenga A, Megna A S, Tinessa V. Alpha-fetoprotein and ultrasonography screening for hepatocellular carcinoma. Gastroenterology 2004; 127:S108-112.
14. Tateishi R, Shiina S, Yoshida H, Teratani T, Obi S, Yamashiki N, Akamatsu M, et al. Prediction of recurrence of hepatocellular carcinoma after curative ablation using three tumor markers. Hepatology 2006; 44:1518-1527.
15. Colli A, Fraquelli M, Casazza G, Massironi S, Colucci A, Conte D, Duca P. Accuracy of ultrasonography, spiral CT, magnetic resonance, and alpha-fetoprotein in diagnosing hepatocellular carcinoma: a systematic review. Am J Gastroenterol 2006; 101:513-523.
16. Kobata A, Amano J. Altered glycosylation of proteins produced by malignant cells, and application for the diagnosis and immunotherapy of tumours. Immunol Cell Biol 2005; 83:429-439.

17. Dennis J W, Granovsky M, Warren C E. Glycoprotein glycosylation and cancer progression. Biochim Biophys Acta 1999; 1473:21-34.
18. Ward D G, Cheng Y, N'Kontchou G, Thar T T, Barget N, Wei W, Billingham L J, et al. Changes in the serum proteome associated with the development of hepatocellular carcinoma in hepatitis C-related cirrhosis. Br J Cancer 2006; 94:287-292.
19. Callewaert N, Van Vlierberghe H, Van Hecke A, Laroy W, Delanghe J, Contreras R. Noninvasive diagnosis of liver cirrhosis using DNA sequencer-based total serum protein glycomics. Nat Med 2004; 10:429-434.
20. Morelle W, Flahaut C, Michalski J C, Louvet A, Mathurin P, Klein A. Mass spectrometric approach for screening modifications of total serum N-glycome in human diseases: application to cirrhosis. Glycobiology 2006; 16:281-293.
21. Zeng M D, Lu L G, Mao Y M, Qiu D K, Li J Q, Wan M B, Chen C W, et al. Prediction of significant fibrosis in HBeAg-positive patients with chronic hepatitis B by a noninvasive model. Hepatology 2005; 42:1437-1445.
22. Afdhal N H. Biopsy or biomarkers: is there a gold standard for diagnosis of liver fibrosis? Clin Chem 2004; 50:1299-1300.
23. Laroy W, Contreras R, Callewaert N. Glycome mapping on DNA sequencing equipment. Nat Protoc 2006; 1:397-405.
24. Giannini E, Risso D, Testa R. Transportability and reproducibility of the AST/ALT ratio in chronic hepatitis C patients. Am J Gastroenterol 2001; 96:918-919.
25. Silva I S, Ferraz M L, Perez R M, Lanzoni V P, Figueiredo V M, Silva A E. Role of gamma-glutamyl transferase activity in patients with chronic hepatitis C virus infection. J Gastroenterol Hepatol 2004; 19:314-318.
26. Hashimoto S, Asao T, Takahashi J, Yagihashi Y, Nishimura T, Saniabadi A R, Poland D C, et al. alpha1-acid glycoprotein fucosylation as a marker of carcinoma progression and prognosis. Cancer 2004; 101:2825-2836.
27. Yazawa S, Madiyalakan R, Izawa H, Asao T, Furukawa K, Matta K L. Cancer-associated elevation of alpha(1-3)-L-fucosyltransferase activity in human serum. Cancer 1988; 62:516-520.
28. Yazawa S, Asao T, Nagamachi Y, Abbas S A, Matta K L. Tumor-related elevation of serum (alpha 1-3)-L-fucosyltransferase activity in gastric cancer. J Cancer Res Clin Oncol 1989; 115:451-455.
29. Chandrasekaran E V, Jain R K, Matta K L. Ovarian cancer alpha 1,3-L-fucosyltransferase. Differentiation of distinct catalytic species with the unique substrate, 3'-sulfo-N-acetyllactosamine in conjunction with other synthetic acceptors. J Biol Chem 1992; 267:23806-23814.
30. Inaba Y, Ohyama C, Kato T, Satoh M, Saito H, Hagisawa S, Takahashi T, et al. Gene transfer of alpha-1,3-fucosyltransferase increases tumor growth of the PC-3 human prostate cancer cell line through enhanced adhesion to prostatic stromal cells. Int J Cancer 2003; 107:949-957.
31. Weston B W, Hiller K M, Mayben J P, Manousos G A, Bendt K M, Liu R, Cusack J C, Jr. Expression of human alpha(1,3)fucosyltransferase antisense sequences inhibits selectin-mediated adhesion and liver metastasis of colon carcinoma cells. Cancer Res 1999; 59:2127-2135.
32. Mon S, Aoyagi Y, Yanagi M, Suzuki Y, Asakura H. Serum N-acetylglucosaminyltransferase III activities in hepatocellular carcinoma. J Gastroenterol Hepatol 1998; 13:610-619.
33. Song E Y, Kim K S, Kim K A, Kim Y D, Kwon D H, Byun S M, Kim H J, et al. Determination of UDP-N-acetylglucosamine: beta-D-mannoside-1,4-N-acetylglucosaminyltransferase-III in patients sera with chronic hepatitis and liver cirrhosis using a monoclonal antibody. Glycoconj J 2002; 19:415-421.
34. Yao M, Zhou D P, Jiang S M, Wang Q H, Zhou X D, Tang Z Y, Gu J X. Elevated activity of N-acetylglucosaminyltransferase V in human hepatocellular carcinoma. J Cancer Res Clin Oncol 1998; 124:27-30.
35. Ito Y, Miyoshi E, Sakon M, Takeda T, Noda K, Tsujimoto M, Ito S, et al. Elevated expression of UDP-N-acetylglucosamine: alphamannoside beta-1,6 N-acetylglucosaminyltransferase is an early event in hepatocarcinogenesis. Int J Cancer 2001; 91:631-637.
36. Koenderman A H, Koppen P L, Koeleman C A, van den Eijnden D H. N-acetylglucosaminyltransferase III, IV and V activities in Novikoff ascites tumour cells, mouse lymphoma cells and hen oviduct. Application of a sensitive and specific assay by use of high-performance liquid chromatography. Eur J Biochem 1989; 181:651-655.
37. Koenderman A H, Wijermans P W, van den Eijnden D H. Changes in the expression of N-acetylglucosaminyltransferase III, IV, V associated with the differentiation of HL-60 cells. FEBS Lett 1987; 222:42-46.
38. Shim J K, Lee Y C, Chung T H, Kim C H. Elevated expression of bisecting N-acetylglucosaminyltransferase-III gene in a human fetal hepatocyte cell line by hepatitis B virus. J Gastroenterol Hepatol 2004; 19:1374-1387.
39. Liesbeth Desmyter L, Fan Y D, Praet M, Jaworski T, Vervecken W, De Hemptinne B, Contreras R, Chen C. Rating of 0014-induced rat liver fibrosis by blood serum glycomics. Journal of Gastroenterology and Hepatology 2006, in press.

The invention claimed is:
1. A method of detecting early stage hepatocellular carcinoma or a change in the gradation of hepatocellular carcinoma in a mammal, the method comprising:
measuring in a sample of serum or blood plasma obtained from the mammal the ratio between branch alpha (1,3)-fucosylated glycans and bisecting N-acetylglucosamine core alpha (1,6)-fucosylated glycans, and
attributing said ratio with the presence of early stage hepatocellular carcinoma in said mammal when said ratio is statistically different from the same ratio measured in a mammal free of hepatocellular carcinoma.
2. The method according to claim 1 wherein the mammal is a human.
3. The method according to claim 2, further comprising measuring clinical chemistry, histology, and/or imaging parameters in said mammal.
4. The method according to claim 3 wherein the measurement comprises measuring alpha-fetoprotein concentration in the mammal's serum or blood.
5. The method according to claim 1, further comprising measuring clinical chemistry, histology, and/or imaging parameters in said mammal.
6. The method according to claim 5 wherein the measurement comprises measuring the concentration of alpha-fetoprotein in serum or blood of the mammal.
7. A method of detecting early stage hepatocellular carcinoma or a change in gradation of hepatocellular carcinoma in a mammal, the method comprising:
determining, in a sample of serum or blood plasma obtained from the mammal, a ratio between branch alpha (1,3)-fucosylated glycans and bisecting N-acetylglucosamine core alpha (1,6)-fucosylated glycans,
statistically comparing the thus determined ratio with a ratio of branch $\alpha$-(1,3)-fucosylated glycans and bisecting N-acetylglucosamine core alpha (1,6)-fucosylated glycans obtained from samples from mammals free of hepatocellular carcinoma, or a ratio of branch $\alpha$-(1,3)-fucosylated glycans and bisecting N-acetylglucosamine core alpha (1,6)-fucosylated glycans obtained from another sample of serum or blood plasma from the mammal taken at an earlier time point, and correlating the statistically compared ratio with early stage hepatocellular carcinoma in the mammal or a change in gradation of hepatocellular carcinoma in the mammal when said determined ratio is statistically different from the same ratio measured in the mammals free of hepatocellular carcinoma or measured in the other sample of serum or blood plasma taken from the mammal at an earlier time point, so as to detect early stage hepatocellular carcinoma or a change in gradation of hepatocellular carcinoma in the mammal.

\* \* \* \* \*